United States Patent
Palmer

(10) Patent No.: US 12,226,587 B2
(45) Date of Patent: Feb. 18, 2025

(54) PRE-LUBRICATED FEMALE URINARY CATHETER PACKAGE

(71) Applicant: Cure Medical LLC, Newport Beach, CA (US)

(72) Inventor: Tim Palmer, Stillwater, MN (US)

(73) Assignee: CONVATEC, INC., Bridgewater, NJ (US)

( * ) Notice: Subject to any disclaimer, the term of this patent is extended or adjusted under 35 U.S.C. 154(b) by 860 days.

(21) Appl. No.: 17/208,936

(22) Filed: Mar. 22, 2021

(65) Prior Publication Data

US 2021/0290894 A1 Sep. 23, 2021

Related U.S. Application Data

(63) Continuation-in-part of application No. 17/168,017, filed on Feb. 4, 2021, now abandoned, which is a
(Continued)

(51) Int. Cl.
*A61M 25/00* (2006.01)
*A61M 25/01* (2006.01)

(52) U.S. Cl.
CPC ...... *A61M 25/002* (2013.01); *A61M 25/0017* (2013.01); *A61M 25/0111* (2013.01); *A61M 2210/1092* (2013.01)

(58) Field of Classification Search
CPC ............ A61M 25/002; A61M 25/0017; A61M 25/0111; A61M 2025/0046; A61M 2025/0062; A61M 2202/0496; A61M 2210/1085; A61M 2025/0175; A61M 2210/1089; A61M 2210/1078;
(Continued)

(56) References Cited

U.S. PATENT DOCUMENTS 3,114,455 A 12/1963 Claisse et al.
3,149,717 A 9/1964 Castelli
(Continued)

FOREIGN PATENT DOCUMENTS

EP 3685872 B1 1/2024
EP 2423127 B2 2/2024
(Continued)

OTHER PUBLICATIONS

World Intellectual Property Organization, International Search Report for International Application No. PCT/2021/023578, mail date Oct. 25, 2021, 21 total pages.

*Primary Examiner* — Adam Marcetich
(74) *Attorney, Agent, or Firm* — TAFT STETTINIUS HOLLISTER LLP; Ryan O. White; Derek B. Lavender

(57) ABSTRACT

A rigid package or container for a sterile pre-lubricated, ready to use female-length catheter with enhanced gel holders and simple constructions. A main body of the rigid container has a hollow interior which may receive a gel holder defining an inner cavity filled with a lubricating gel. The gel holder partly inserts into the main body and a tube of the catheter inserts through the gel holder into the main body with a proximal outlet projecting out of the gel holder so as to be graspable. Alternatively, the gel may be provided within the hollow interior of the main body. A rigid and closed cap seals to either the main body or the gel holder and closes the hollow interior of the main body.

21 Claims, 29 Drawing Sheets

Related U.S. Application Data continuation of application No. 16/827,276, filed on Mar. 23, 2020, now Pat. No. 10,912,918.

(58) Field of Classification Search
CPC .......... A61M 2210/1092; A61M 5/346; A61M 2207/00; A61M 25/01; A61M 5/002; A61M 2025/0004; B65D 81/22
See application file for complete search history.

(56) References Cited

U.S. PATENT DOCUMENTS

| | | | |
|---|---|---|---|
| 3,229,813 A | | 1/1966 | Crowe et al. |
| 3,861,395 A | | 1/1975 | Tokudo |
| 3,967,728 A | | 7/1976 | Gordan et al. |
| 4,246,909 A | * | 1/1981 | Wu .................... A61M 25/002 600/580 |
| 4,622,033 A | | 11/1986 | Taniguchi |
| 4,811,847 A | | 3/1989 | Reif et al. |
| 6,053,905 A | | 4/2000 | Daignault et al. |
| 6,090,075 A | | 7/2000 | House |
| 6,382,223 B1 | * | 5/2002 | Lah ........................ E04H 15/60 52/848 |
| 6,578,709 B1 | | 6/2003 | Kavanagh |
| 6,602,244 B2 | | 8/2003 | Kavanahg et al. |
| 6,634,498 B2 | | 10/2003 | Kayerod et al. |
| 6,638,269 B2 | | 10/2003 | Wilcox |
| 8,181,778 B1 | | 5/2012 | van Groningen et al. |
| 8,317,775 B2 | | 11/2012 | House |
| 8,579,115 B2 | | 11/2013 | Murphy et al. |
| 8,668,683 B2 | | 3/2014 | Golden |
| 9,220,866 B2 | | 12/2015 | van Groningen et al. |
| 9,687,629 B1 | | 6/2017 | Palmer |
| 11,980,721 B2 | | 5/2024 | Hilton et al. |
| 11,980,732 B2 | | 5/2024 | Hesse |
| 11,998,705 B2 | | 6/2024 | Schertiger et al. |
| 2003/0018302 A1 | | 1/2003 | Kavanagh |
| 2003/0018322 A1 | * | 1/2003 | Tanghoj ............... A61M 25/002 604/544 |
| 2004/0158231 A1 | * | 8/2004 | Tanghoj ............ A61M 25/0067 604/544 |
| 2006/0263404 A1 | | 11/2006 | Nielsen et al. |
| 2008/0172042 A1 | | 7/2008 | House |
| 2008/0183191 A1 | | 7/2008 | Kevin et al. |
| 2008/0228258 A1 | * | 9/2008 | Gerdts ....................... A61F 2/95 604/533 |
| 2012/0110951 A1 | | 5/2012 | Van Groningen et al. |
| 2012/0316515 A1 | * | 12/2012 | Terry .................. A61M 25/007 604/257 |
| 2013/0292286 A1 | | 11/2013 | Van Groningen et al. |
| 2014/0148795 A1 | * | 5/2014 | Tanghoej .......... A61M 25/0017 604/544 |
| 2014/0276661 A1 | * | 9/2014 | Hannon ............. A61M 25/0113 604/544 |
| 2015/0231377 A1 | * | 8/2015 | Tierney ............. A61M 25/0074 604/544 |
| 2016/0213880 A1 | * | 7/2016 | O'Flynn ............. A61M 25/002 |
| 2018/0161539 A1 | | 6/2018 | Palmer |
| 2021/0100979 A1 | * | 4/2021 | Donnelly ........... A61M 25/0111 |
| 2021/0170140 A1 | * | 6/2021 | Owen ................. A61M 25/002 |
| 2024/0008968 A1 | | 1/2024 | Conway et al. |
| 2024/0033478 A1 | | 2/2024 | O'Flynn et al. |
| 2024/0058569 A1 | | 2/2024 | McMenamin et al. |
| 2024/0108850 A1 | | 4/2024 | Yin et al. |

FOREIGN PATENT DOCUMENTS

| | | |
|---|---|---|
| EP | 4324616 A2 | 2/2024 |
| EP | 3713632 B1 | 3/2024 |
| EP | 4338784 A2 | 3/2024 |
| EP | 3503934 B1 | 6/2024 |
| WO | 03008028 A2 | 1/2003 |
| WO | 012060699 A1 | 5/2012 |

\* cited by examiner

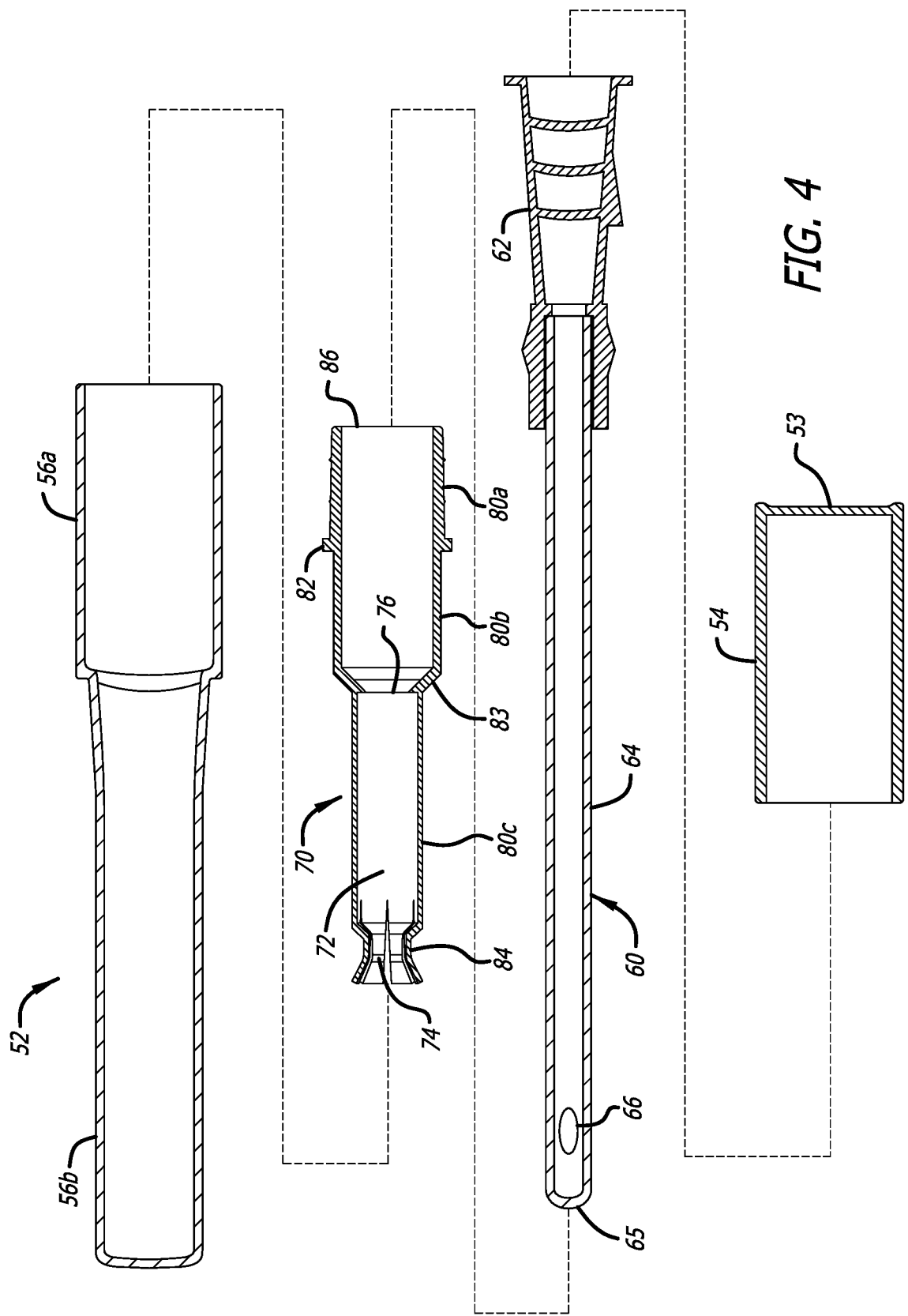

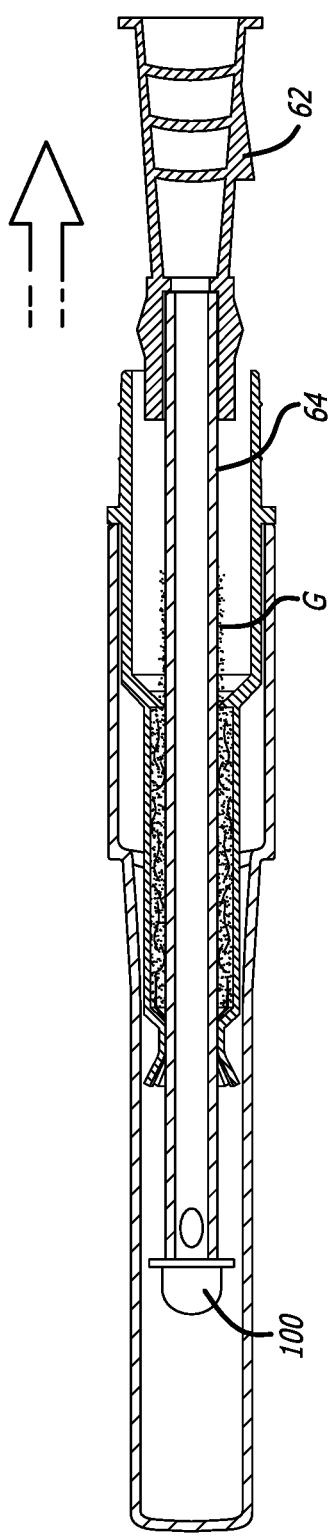
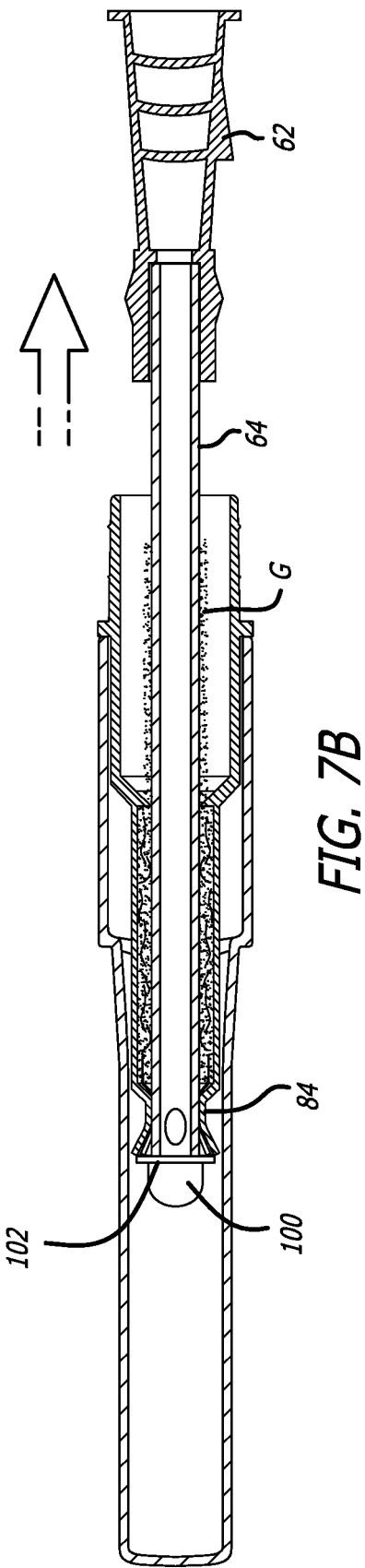
FIG. 7A
FIG. 7B

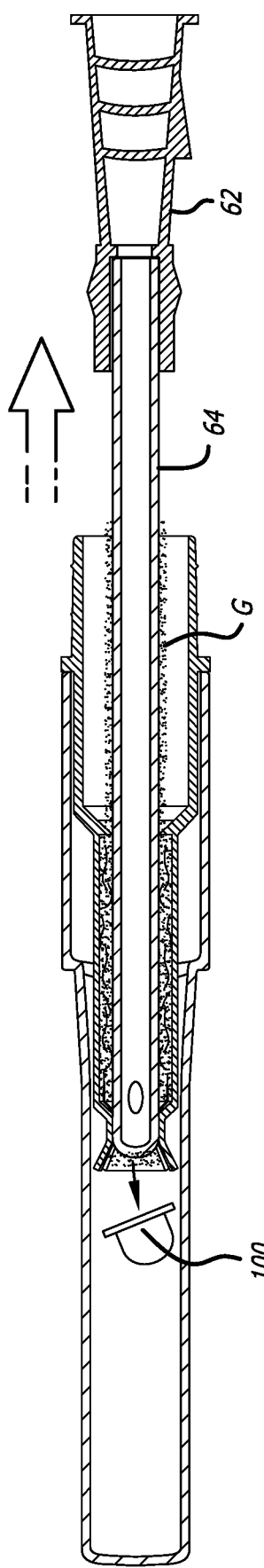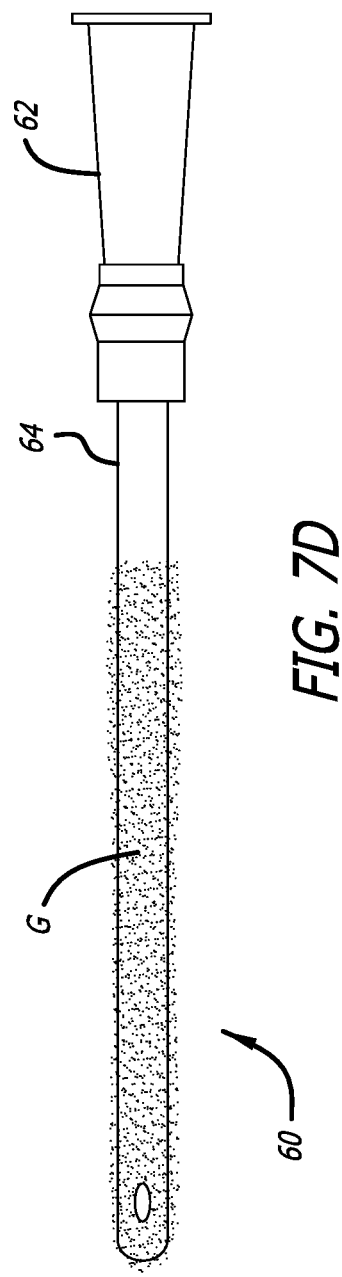
FIG. 7C
FIG. 7D

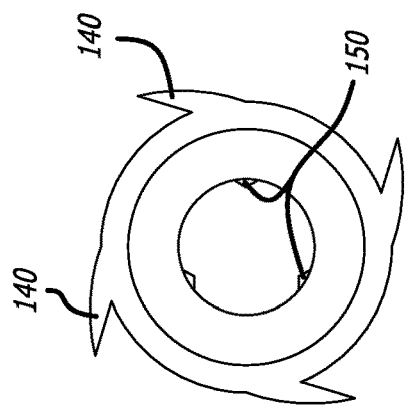
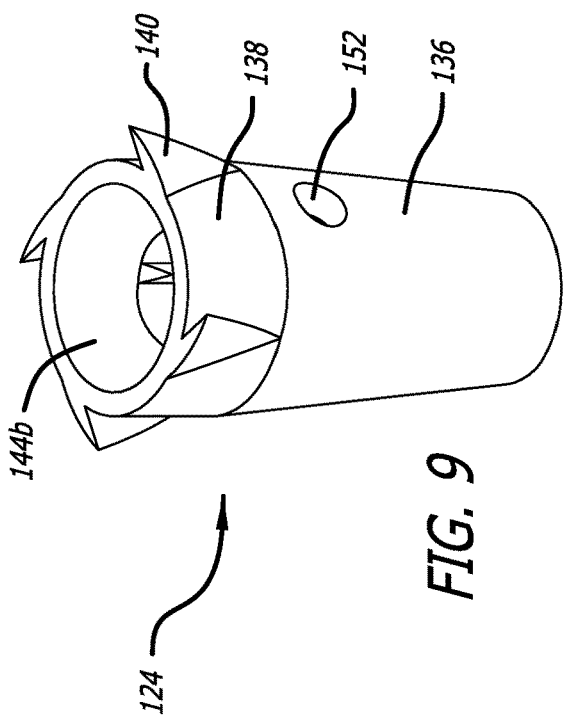
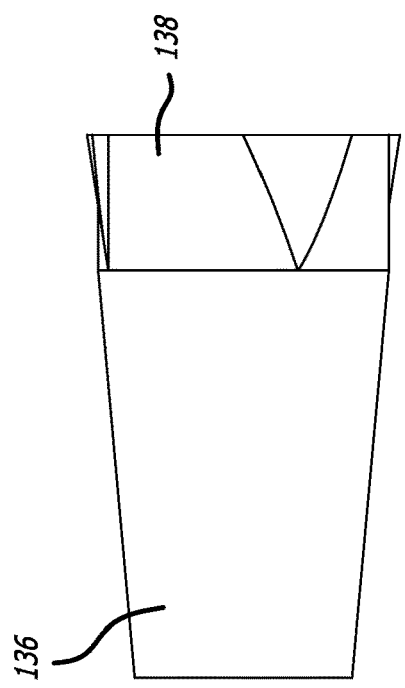
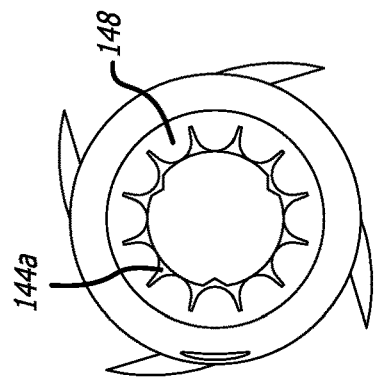

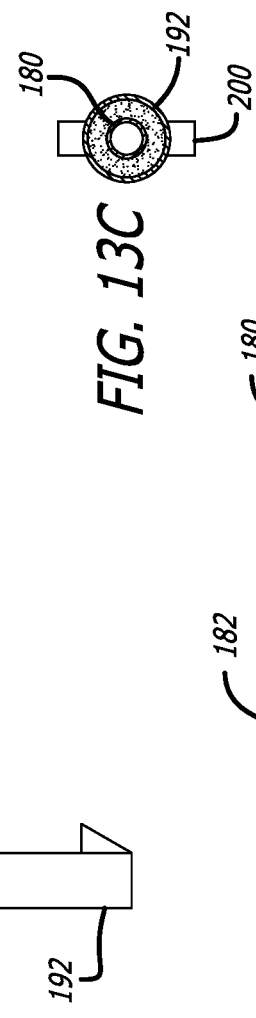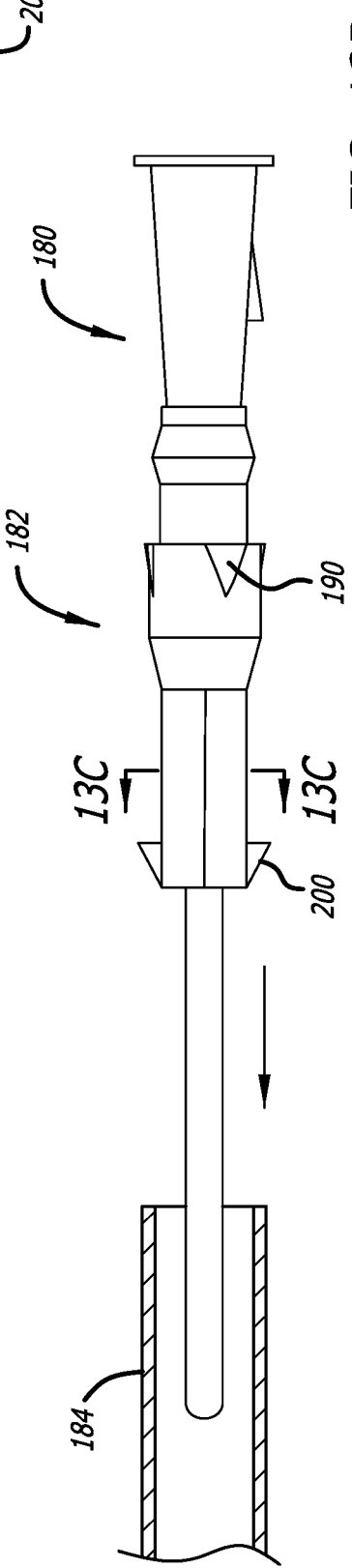

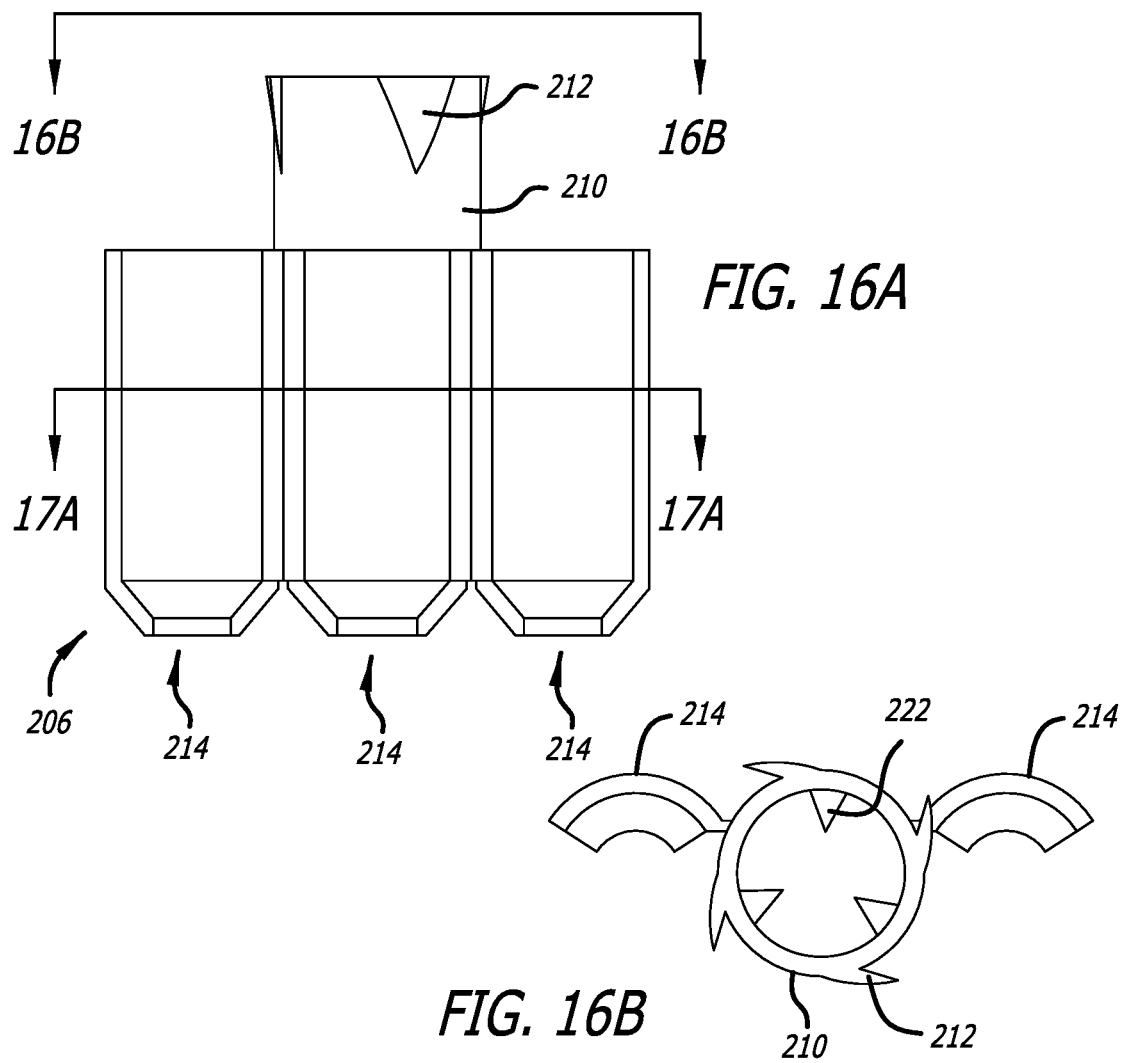
FIG. 16A
FIG. 16B
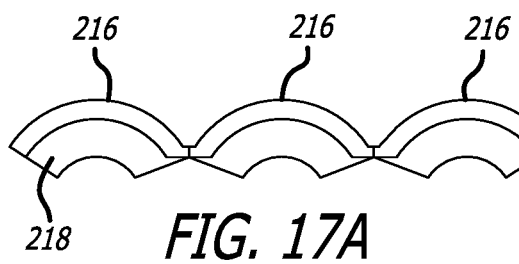
FIG. 17A
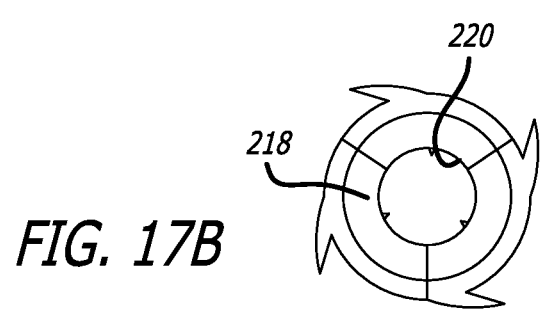
FIG. 17B

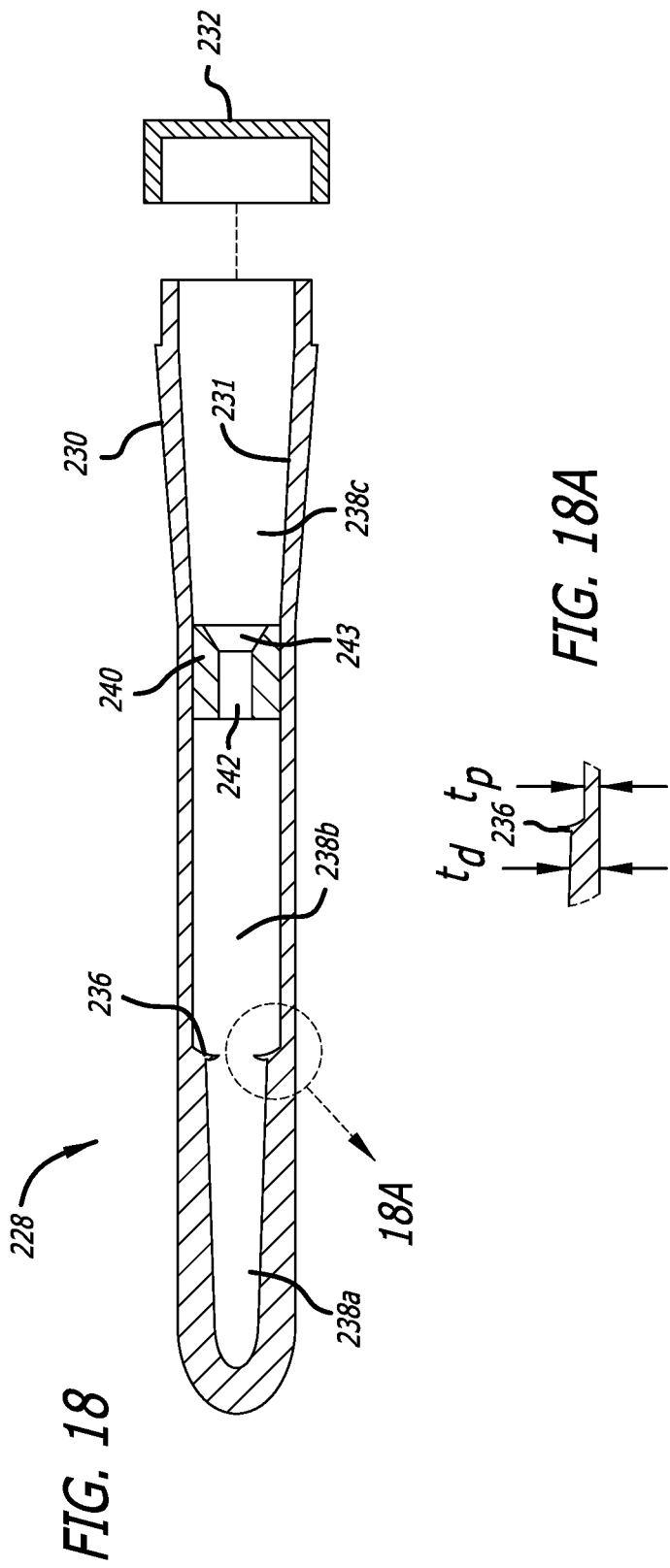
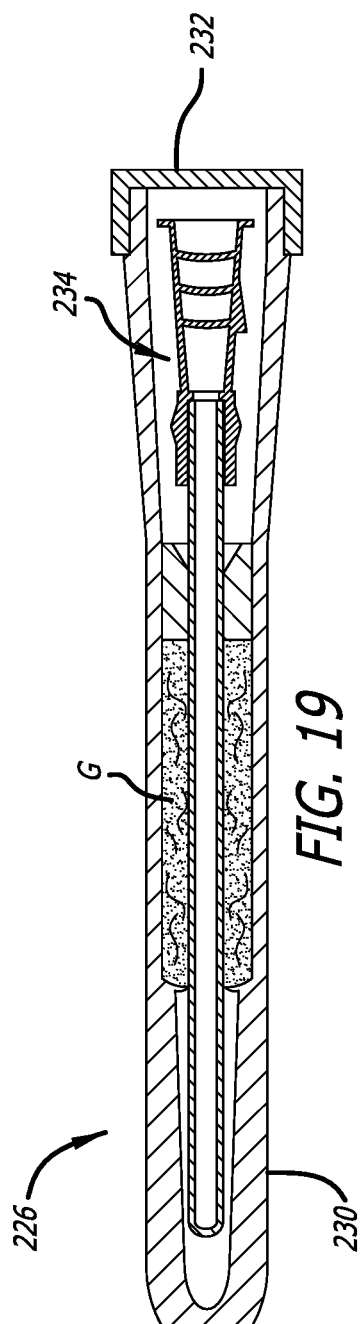
FIG. 18
FIG. 18A
FIG. 19

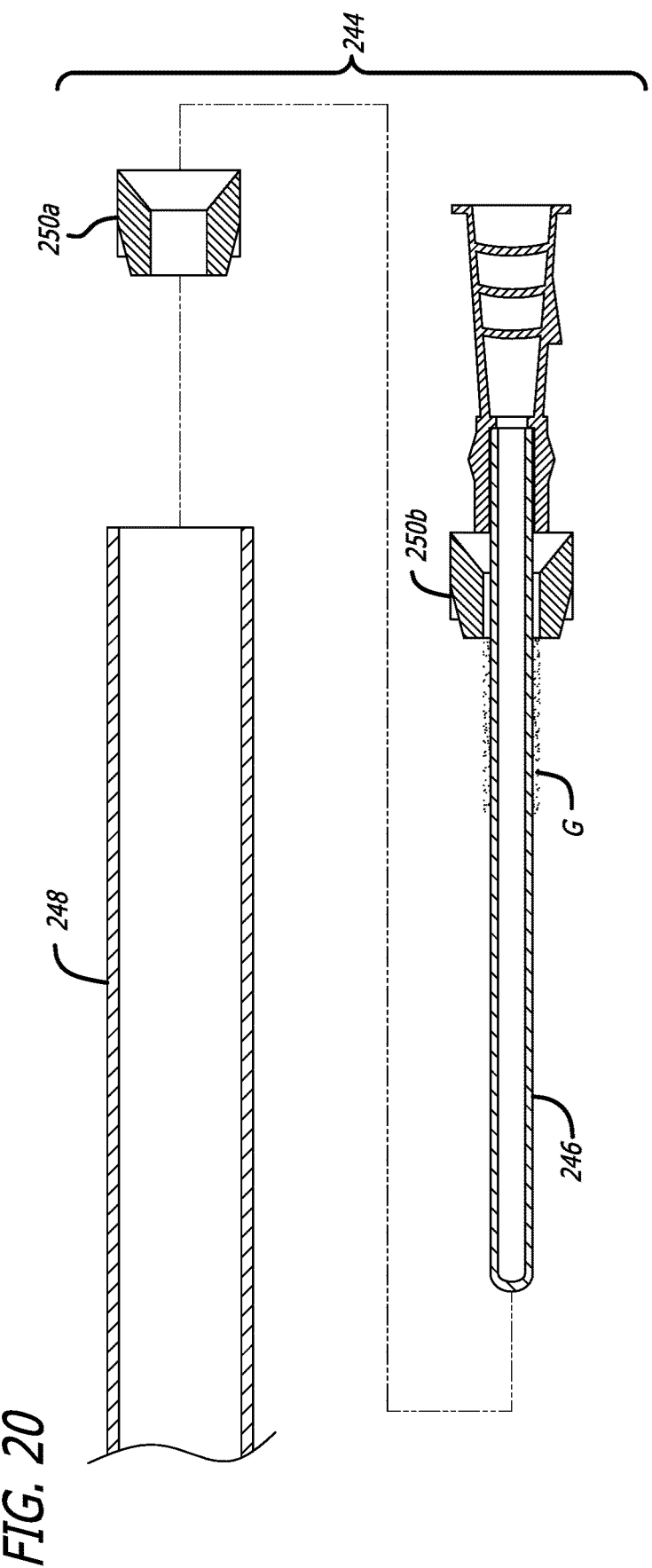

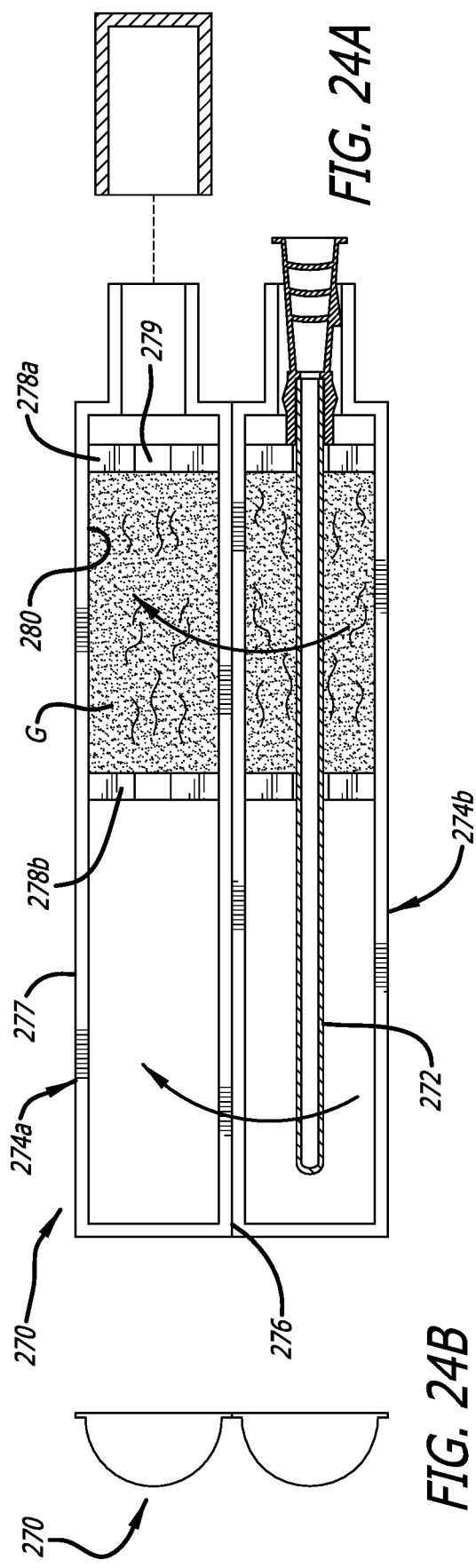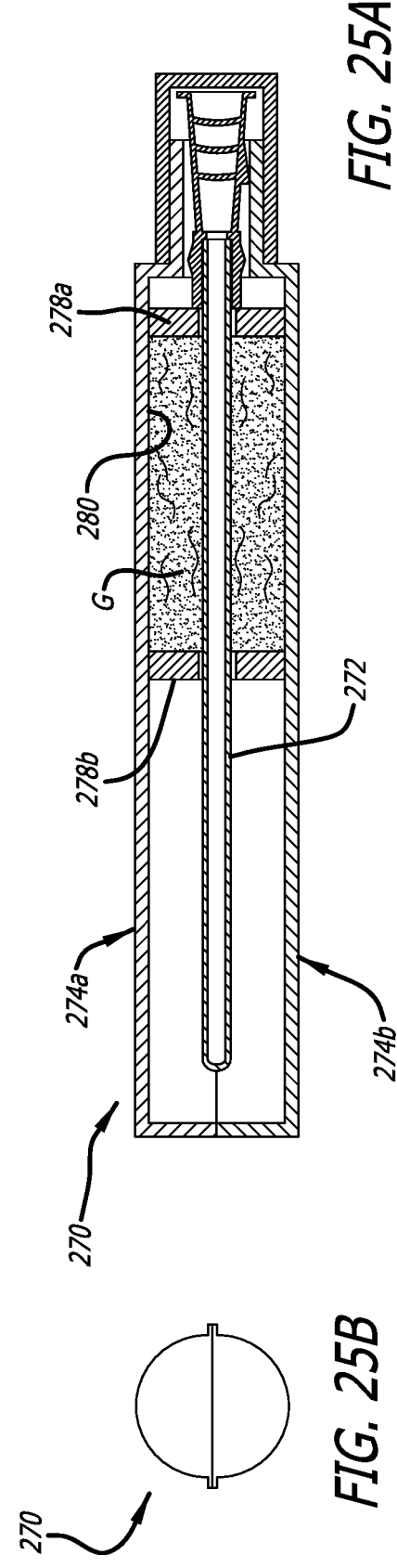

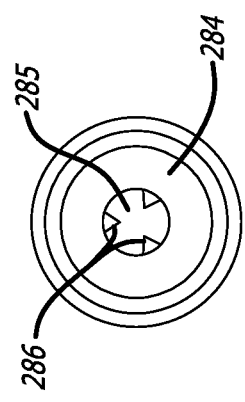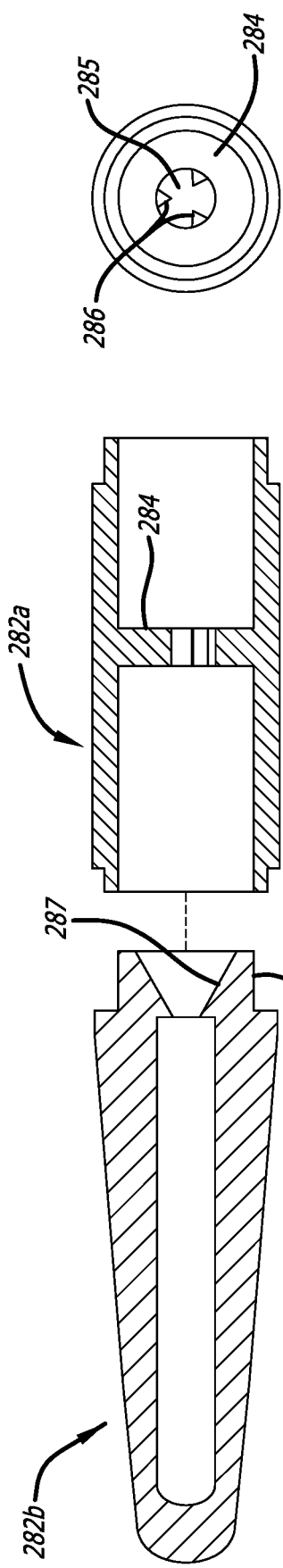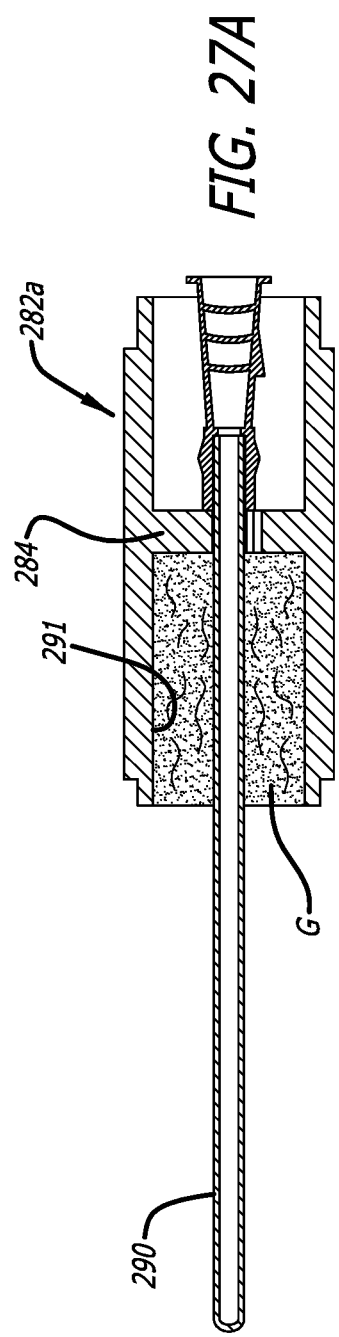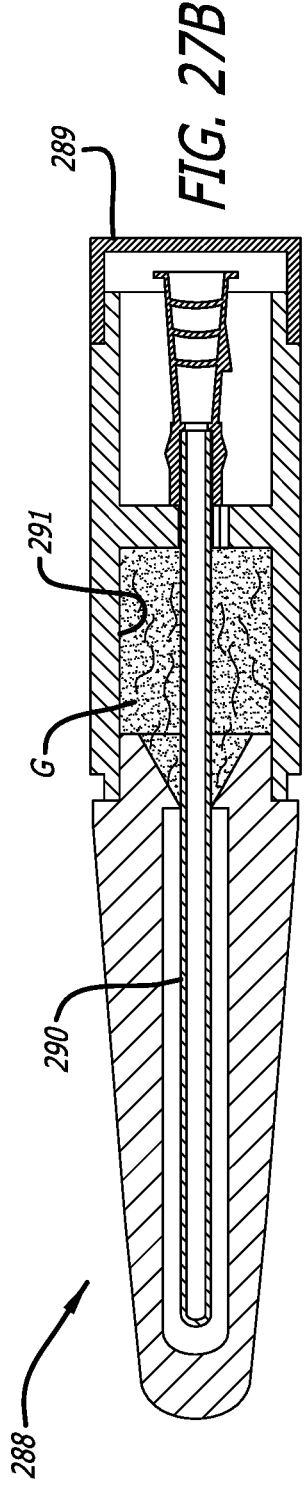

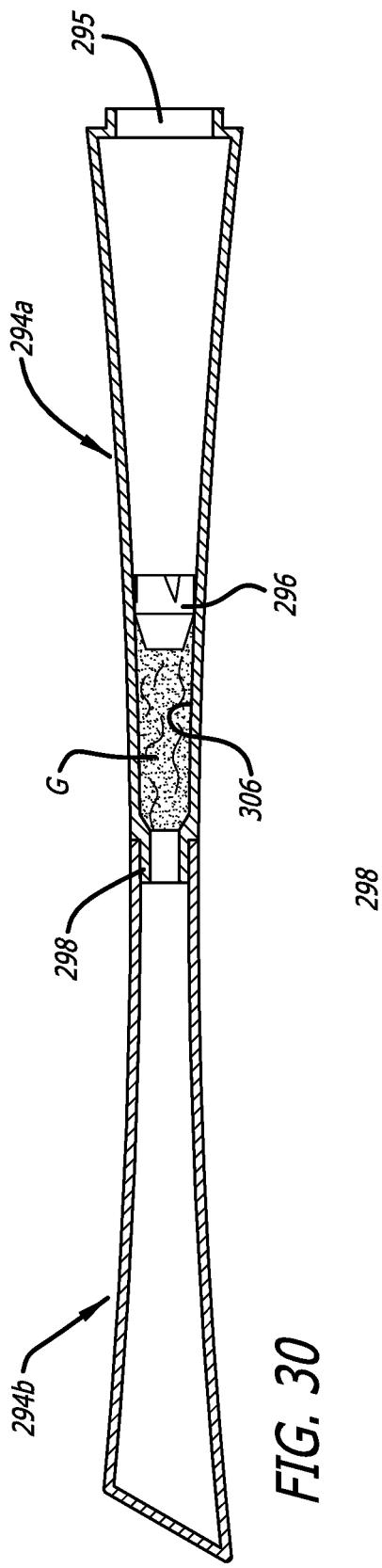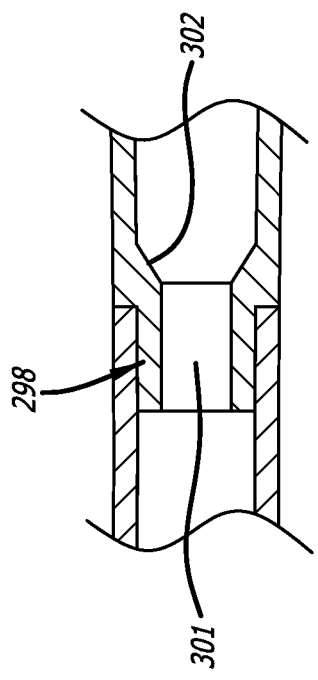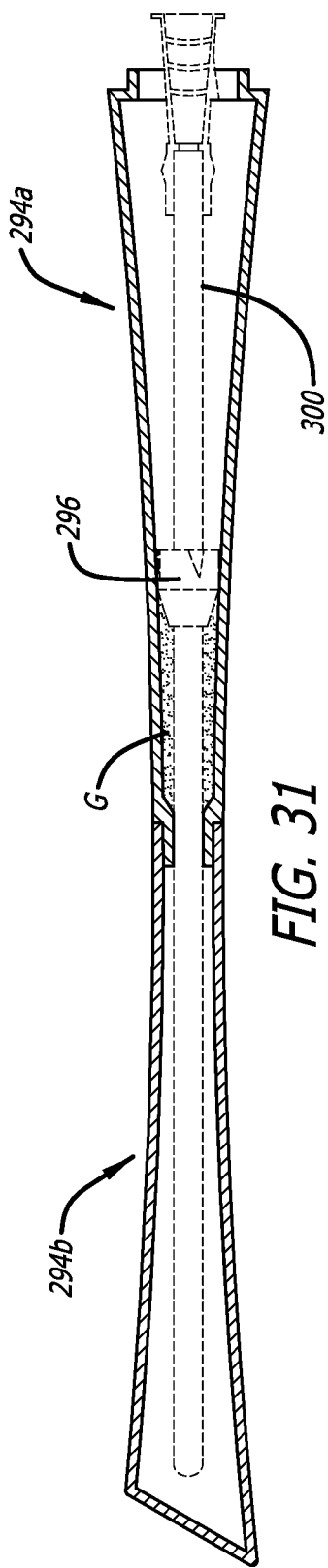

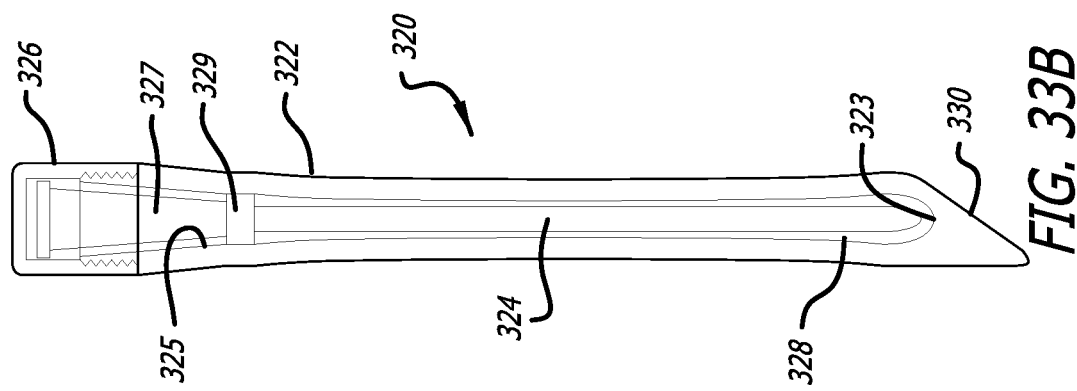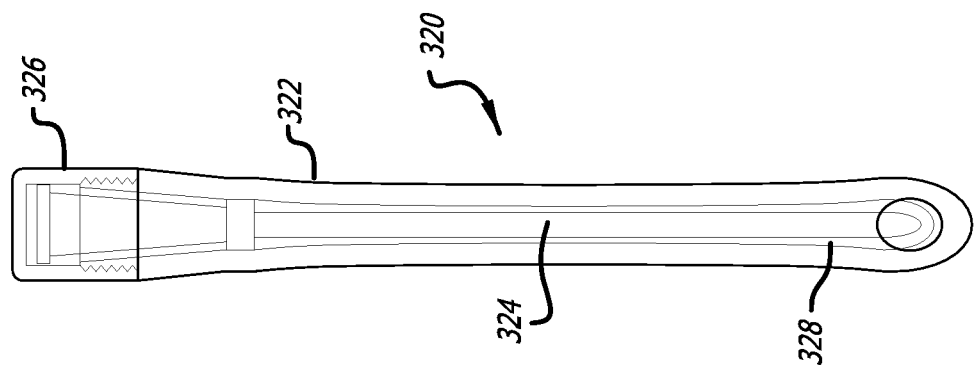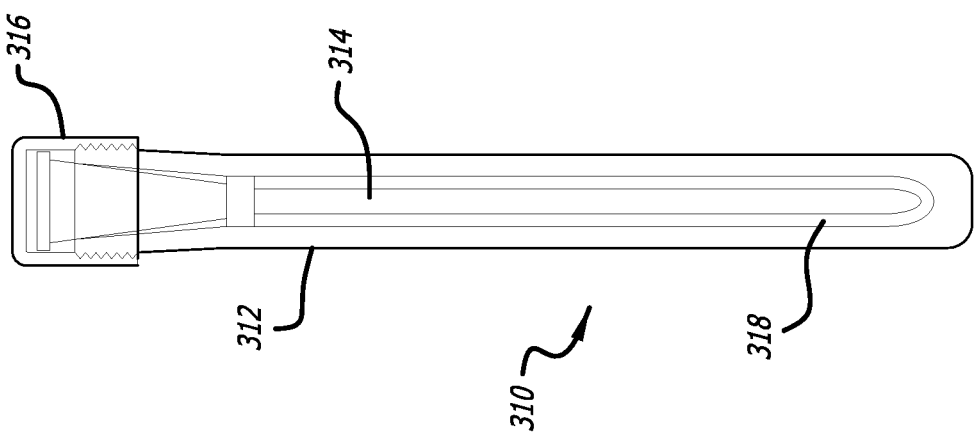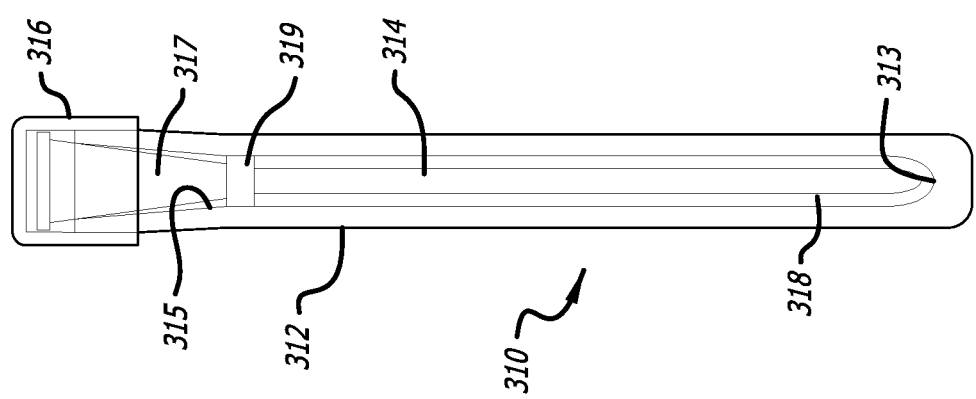

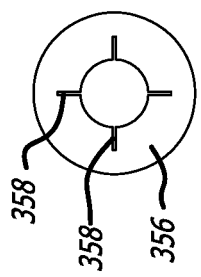
FIG. 36A
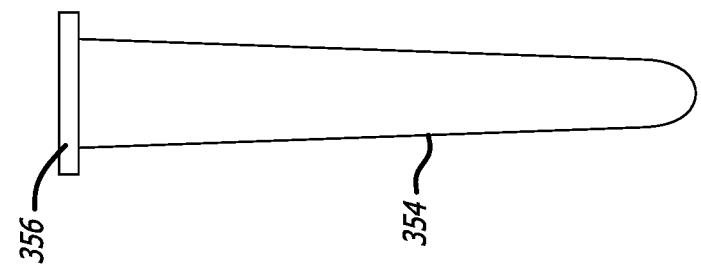
FIG. 36B
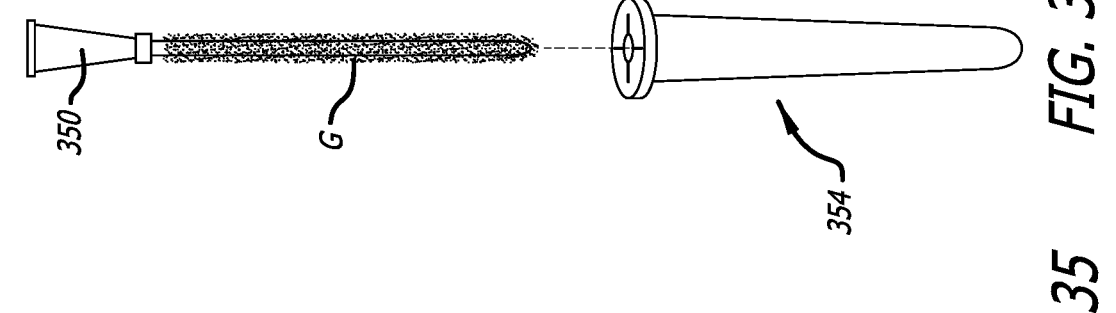
FIG. 36
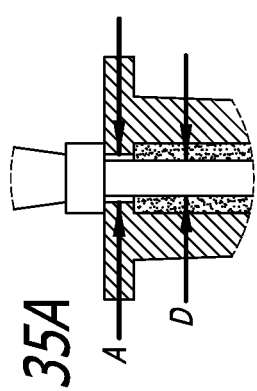
FIG. 35A
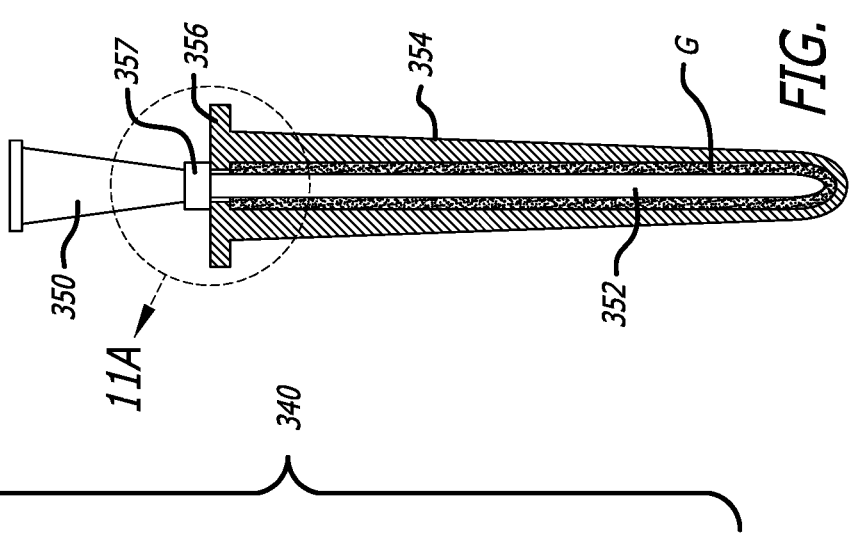
FIG. 35
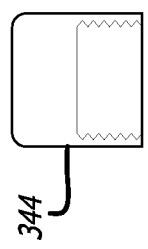
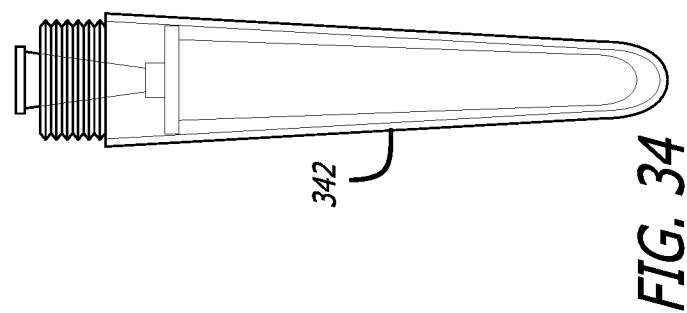
FIG. 34

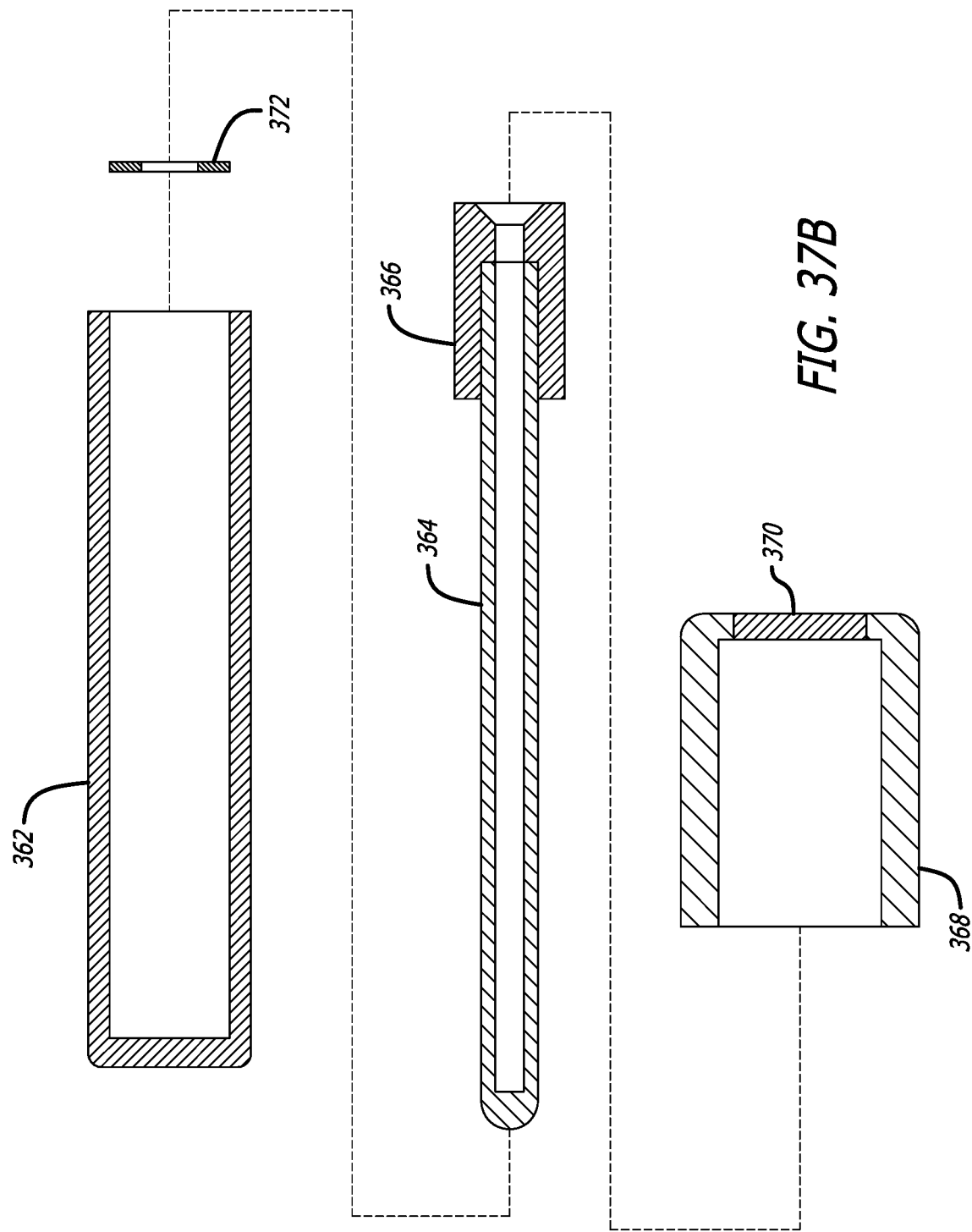

PRE-LUBRICATED FEMALE URINARY CATHETER PACKAGE

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner have no objection to the facsimile reproduction by anyone of the patent disclosure as it appears in the Patent and Trademark Office patent files or records, but otherwise reserves all copyright and trade dress rights whatsoever.

RELATED APPLICATIONS

The present application is a continuation-in-part of U.S. patent application Ser. No. 17/168,017 filed Feb. 4, 2021, which is a continuation of U.S. patent application Ser. No. 16/827,276, filed Mar. 22, 2020 now U.S. Pat. No. 10,912,918, the contents of which are hereby expressly incorporated by reference.

FIELD

The present application relates to a sterile rigid package housing a female pre-lubricated urinary catheter which can be used for (intermittent) self-catheterization by a patient.

BACKGROUND

Intermittent catheters are typically used by patients suffering from urinary incontinence or by individuals unable to have voluntary urination. In our highly mobile culture, the ability to have the freedom to leave home for the day or longer is an important part of life. To accommodate this need, single use catheters have been developed to allow patients to perform self-catheterization.

A gel container is used as a means to apply gel to a urinary catheter upon withdrawal of the catheter from a package. Typically, the gel container is made of a flexible material like molded silicone. If the container is assembled into a rigid package there is no way for the user to manipulate the container to ensure adequate gel coverage of the distal (tip) end of the catheter.

Urinary catheters come in different lengths depending on the user: There are conventionally three lengths: female (12-26 cm), standard for men (40-45 cm) and pediatric (30-31 cm).

The Cure Twist available from Cure Medical of Newport Beach, CA is a compact female length catheter packaged in a rigid tube package with an internal, flexible gel holder molded of silicone rubber. To help reduce the stigma of having to use the catheter, the Twist package is relatively short and conveniently resembles a tube for cosmetics, such as eyeliner. The gel holder provides a cavity for lubricating gel in storage and applies it to the catheter tubing as the catheter is withdrawn from the package. U.S. Pat. No. 8,181,778 discloses such a rigid container for a catheter having a shortened tube with a leading end and a proximal end provided with a catheter outlet or connector. U.S. Pat. No. 9,687,629 discloses alternative gel holders which are shaped so as to ensure gel covers the extreme distal tip of the catheter. The user removes the catheter for use, either by joining the connector to a collection bag or other collection device or by simply using the catheter while sitting on the toilet. The catheter is lubricated and ready to use directly from the package.

Though the Cure Twist packaged catheter is convenient and surreptitious, it includes a number of components that raise its price, and thus there is a need for a similar product which is simpler and thus less expensive to make.

SUMMARY OF THE INVENTION

Embodiments of the present invention seek to provide an enhanced package for a urinary catheter, suitable for everyday use by a patient.

In one embodiment, a package or container consists essentially of a rigid generally tubular main body, a urinary catheter and a rigid cap. The main body has a distal closed end and a proximal open mouth and defines within a hollow interior. The urinary catheter has an elongated flexible tube defining a closed distal tip with one or more flow openings formed in an adjacent sidewall thereof, and a proximal outlet attached to a proximal end of the tube and having a through-bore in communication with a lumen of the tube. The tube of the urinary catheter is inserted through the open mouth of the main body and into the hollow interior such that at least a portion of the outlet remains outside the main body. An outer diameter of the tube is less than an inner diameter of the hollow interior so that a concentric space is formed therebetween which is at least partly filled with a lubricating gel to the distal closed end of the main body such that lubricating gel remains on the catheter tube when the tube is retracted from within the main body. The rigid cap secures to the open mouth of the main body, and the rigid cap is solid without openings so as to seal the urinary catheter within the hollow interior in a sterile manner.

The rigid cap is preferably secured to the open mouth of the main body with mating threads. The generally tubular main body may have a shallow hourglass shape that narrows in a middle portion and the lubricating gel is deposited only in a distal end of the hollow interior of the main body to limit the amount of gel that remains on the catheter tube when retracted from within the main body.

The urinary catheter package may further including a bulkhead or divider wall secured within the main body and having a central aperture sized slightly larger than the catheter tube. The divider wall segregates the hollow interior of the main body into a proximal first section and a distal second section, wherein the lubricating gel is deposited only in the distal second section. A diameter D of the catheter tube preferably ranges between about 2.7-5.3 mm, and a diameter A of the central aperture is about 1-2 mm larger than the diameter D. The divider wall may be formed by a molded bulkhead within the main body, or may be a removable annular disk retained within the inside of the main body with adhesive or held in place by a snap fit into a ring-shaped receiving cavity.

A second embodiment of urinary package or container consists essentially of a rigid generally tubular main body, a gel holder, a urinary catheter and a rigid cap. The main body has a distal closed end and a proximal open mouth and defining within a hollow interior. The gel holder has a distal section defining an inner cavity at least partly filled with a lubricating gel and a proximal section. The distal section has a distal opening and a proximal opening leading to the proximal section, and the proximal section has an open proximal end. The gel holder is inserted through the open mouth of the main body and into the hollow interior, and the gel holder has an outer circumferential rib at one end of the proximal section that is sized to interfere with the open mouth such that the proximal section remains outside the hollow interior of the main body. The urinary catheter has an elongated flexible tube defining a closed distal tip with one or more flow openings formed in an adjacent sidewall thereof, and a proximal outlet attached to a proximal end of the tube and having a throughbore in communication with a lumen of the tube. The tube of the urinary catheter is inserted first into the open proximal end of the proximal section and extends through the entire gel holder such that the distal tip extends past the distal opening of the distal section and is within the hollow interior of the main body and at least a portion of the outlet remains outside the main body. A concentric space is formed around the tube within the distal section of the gel holder such that lubricating gel remains on the catheter tube when the tube is retracted from within the gel holder. The rigid cap secures to the proximal section of the gel holder, the rigid cap being solid without openings so as to seal the urinary catheter within the hollow interior in a sterile manner.

The package of the second embodiment may further include a gel cap filled with gel that fits over the distal tip of the catheter tube, the gel cap being larger than the distal opening of the distal section so that it falls off the end of the tube when the tube is retracted from within the gel holder. The gel cap may have a hemispherical cup-shaped body and an outer flange that is larger than the distal opening of the distal section. The distal opening of the distal section of the gel holder may be defined by a plurality of cantilevered fingers separated by longitudinal slots, and the gel holder is molded of a flexible polymer which permits introduction of the lubricant gel into the inner cavity by inserting a syringe or other similar implement between the catheter tube and the cantilevered fingers which flex outward. The longitudinal slots preferably commence along the distal section and gradually widen toward the distal ends of the cantilevered fingers. In one version the cantilevered fingers are molded to constrict a distal end of the distal section, then extend a short linear distance within which is defined the distal opening, before flaring outward to distal ends of the cantilevered fingers.

The proximal section of the gel holder may have a diameter that is approximately the same as an inner luminal diameter of the rigid cap such that the rigid cap is secured to the proximal section with an interference fit. The proximal section may have a pair of external axially-spaced ribs that interfere with the inner luminal diameter of the rigid cap so as to retain and seal it on the proximal section. In one embodiment, the proximal section is molded with a slight narrowing taper toward the proximal opening and a proximal rib is sized larger than a distal rib so as to have about the same diameter. The ribs may be triangular and asymmetric in cross-section with a steeper proximal face than a distal face.

One embodiment of a urinary catheter package with internal barriers comprises a rigid generally tubular main body having a distal closed end opposite a proximal open mouth along a longitudinal axis and defining within a hollow interior. A pair of spaced apart internal barriers including a distal barrier and a proximal barrier are both positioned within the main body. The internal barriers extend transversely across the hollow interior and define a gel cavity therebetween for receiving lubricating gel. Each barrier has a central throughbore sized to permit passage of the tube of the catheter, with the throughbore of the distal barrier being sized approximately the same as the tube to substantially prohibit gel from passing distally past the distal barrier. The tube of the urinary catheter may be inserted through the open mouth of the main body and into the hollow interior through both barriers such that at least a portion of the proximal outlet remains outside the main body, and such that the urinary catheter may be withdrawn from the main body and lubricating gel from the gel cavity remains on the tube. A rigid cap secures to the open mouth of the main body so as to seal the urinary catheter within the hollow interior in a sterile manner.

The internal barriers may both formed by molded walls within the main body/In one version, the main body is formed by two longitudinal halves brought together and sealed around their contacting edges, each half forming part of each barrier. The two halves may be molded as a single piece with a living hinge therebetween. Alternatively, the main body is formed by a proximal component coupled in series to a distal component, wherein the proximal barrier is formed by a transverse wall within a midsection of the proximal component and the distal barrier is formed by an entry aperture at a proximal end of the distal component leading to a hollow cavity in the distal component.

In another version, the internal barriers are both formed by inserts separate from the main body. For instance, the inserts may comprise generally tubular members, wherein external structural features of the tubular members and/or internal structural features of an inner wall of the main body are configured so that the tubular members may be inserted to predetermined spaced-apart depths within the hollow interior.

The distal barrier may be formed by a molded feature within the main body while the proximal barrier is formed by an insert separate from the main body. External structural features of the insert that forms the proximal barrier and/or internal structural features of an inner wall of the main body are desirably configured so that the insert may be inserted to a predetermined depth within the hollow interior spaced from the distal barrier. For instance, the inner wall of the main body tapers inward from the proximal open mouth in a distal direction such that the insert may be pressed into the hollow interior to the predetermined depth before interference between the insert and the inner wall halts further advancement.

The main body may be formed by a proximal component coupled in series to a distal component at a junction, wherein the distal barrier is formed by a narrowing at the junction leading to a hollow cavity in the distal component. The insert may be a generally tubular member, wherein external structural features of the tubular member and/or internal structural features of an inner wall of the main body are configured so that the tubular member may be inserted to predetermined depth within the hollow interior spaced apart from the molded feature that forms the distal barrier.

The proximal and distal barriers preferably have a tapered lead-in to the throughbores therein. The proximal barrier may have a plurality of inwardly-projecting axial ribs within the throughbore therein that contact and center the tube of the catheter and ensure an even layer of gel is applied to the tube upon withdrawal past the proximal barrier.

The catheter of either embodiment may have a length of between about 10-15 cm, and the catheter package has a length of no more than 1-2 cm longer than the catheter.

BRIEF DESCRIPTION OF THE DRAWINGS

FIG. 4 is an exploded view of the components thereof;

FIGS. 7A-7D show several steps in removal of the catheter tube from within the rigid container shown in FIG. 6, with the end result being complete coverage of the catheter tube with lubricant gel;

FIG. 9 is a perspective view of the gel holder for the urinary catheter of FIG. 8;

FIGS. 9A-9C are orthogonal views of the gel holder of FIG. 9;

FIG. 13A is a side view showing a pre-assembly of a urinary catheter with the foldable gel holder of FIGS. 14A-14C, FIG. 13B is a side view of an assembly of the urinary catheter with gel holder being inserted into a rigid main body of a sterile container, and FIG. 13C is a sectional view through the gel holder folded around the urinary catheter;

FIGS. 16A and 16B are front elevational and top plan views, respectively, of the foldable gel holder of FIGS. 15A and 15B, FIG. 17A is a sectional view through a midportion of the gel holder indicating a folding operation, and FIG. 17B is an end view of the folded gel holder;

FIG. 18 is a longitudinal sectional view through a sterile container for a urinary catheter having internal spaced bulkheads defining an inner gel cavity, and FIG. 18A is an enlargement of the side of a rigid main body of the sterile container showing a distal bulkhead molded therein;

FIG. 19 is a longitudinal sectional view of the sterile container of FIG. 18 with a urinary catheter stored therein and gel placed in the inner cavity between the bulkheads;

FIG. 20 is an exploded side view of a still further sterile container along with a urinary catheter in a pre-assembled configuration, and FIG. 21 is a longitudinal sectional view through the sterile container and urinary catheter assembled;

FIGS. 24A and 24B are top plan and end elevational views of a clamshell-type of sterile container showing the urinary catheter and gel placed therein in a pre-assembled configuration;

FIGS. 25A and 25B are top plan and end elevational views of the assembled clamshell-type sterile container and urinary catheter of FIG. 24A;

FIG. 26A is an exploded longitudinal sectional view of two components of a rigid main body of a urinary catheter sterile container, and FIG. 26B is an end elevational view of a proximal component thereof;

FIG. 27A is a longitudinal sectional view of the proximal component of the rigid main body of FIG. 26A pre-assembled with a urinary catheter and lubricating gel, and FIG. 27B shows the addition of a distal component and a sterile end cap;

FIG. 30 is a longitudinal sectional view of the two-part rigid main body of the sterile container of FIG. 29, and FIG. 30A is an enlargement of a distal bulkhead thereof;

FIG. 31 is a side view of the sterile container of FIG. 29 shown assembled with a urinary catheter, proximal bulkhead, and sterile end cap;

FIGS. 32A-32B are side elevational views of two different sterile containers for intermittent urinary catheters;

FIGS. 33A-33B are side elevational views of a further sterile container for intermittent urinary catheters;

FIG. 34 is a side elevational view of an alternative sterile container for an intermittent urinary catheter;

FIG. 35 is a sectional view through a gel holder which receives a catheter tube for use in the sterile container of FIG. 34, and FIG. 35A is an enlarged view of an open end of the gel holder and catheter;

FIG. 36 is an exploded view of the catheter tube removed from the gel holder of FIG. 36 showing complete coverage of the catheter tube with lubricant gel;

FIGS. 36A and 36B are orthogonal views of the gel holder of FIG. 36;

FIGS. 37A-37B are exploded views of alternative configurations of the components of the sterile container of FIG. 37.

DETAILED DESCRIPTION OF A PREFERRED EMBODIMENT

The present application provides an easy to use and easy to carry solution for providing a medical device in the form of a catheter.

Figure 1:
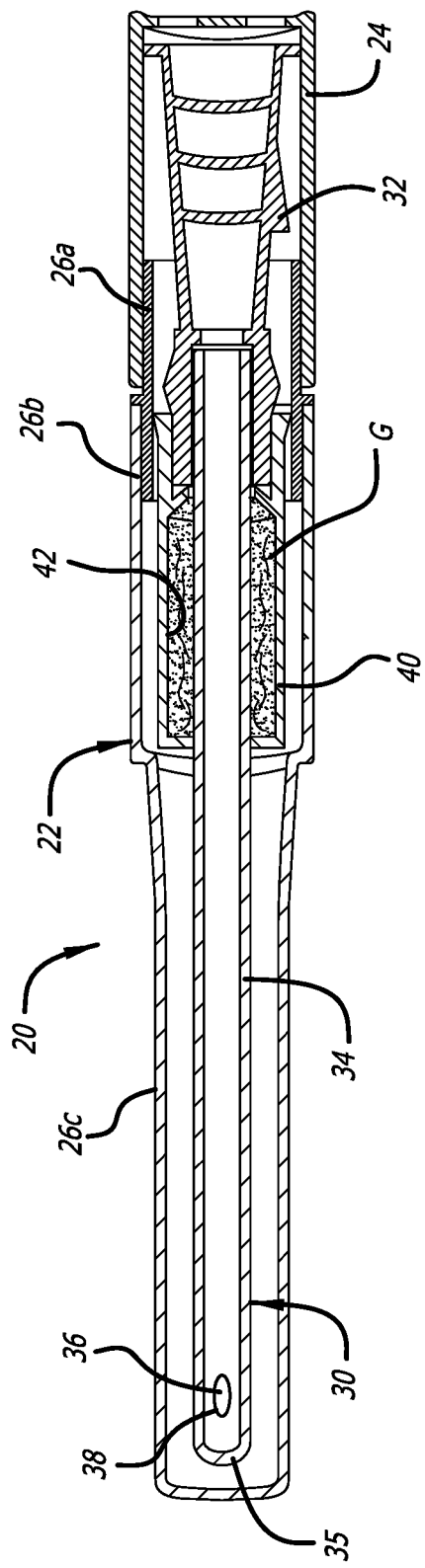
FIG. 1 is a longitudinal sectional view through a sterile container of the prior art for an intermittent urinary catheter.

FIG. 1 illustrates a cross sectional view of a prior art intermittent catheter container 20 such as shown in U.S. Pat. No. 8,181,778, with all elements assembled. Catheter container 20 includes a pen-like rigid and generally hollow tubular main body 22 which is closed off at a distal end 23 thereof, and which can be closed off at a proximal, open end using a cap 24.

The cross-sectional view of main body 22 shows a proximal first part 26a, a middle second part 26b and distal third part 26c, which have respective diameters as described in U.S. Pat. No. 8,181,778. It should be noted that the direction "proximal" is defined as the direction in which a urinary catheter 30 is withdrawn from the main body 22. Preferably, first part 26a has a first inner diameter which is less than second inner diameter of second part 26b, and third part 26c has a third inner diameter which is less than second inner diameter of second part 26b. In other words, the middle second part 26b has a larger diameter than either of the proximal or distal parts.

Figure 2:
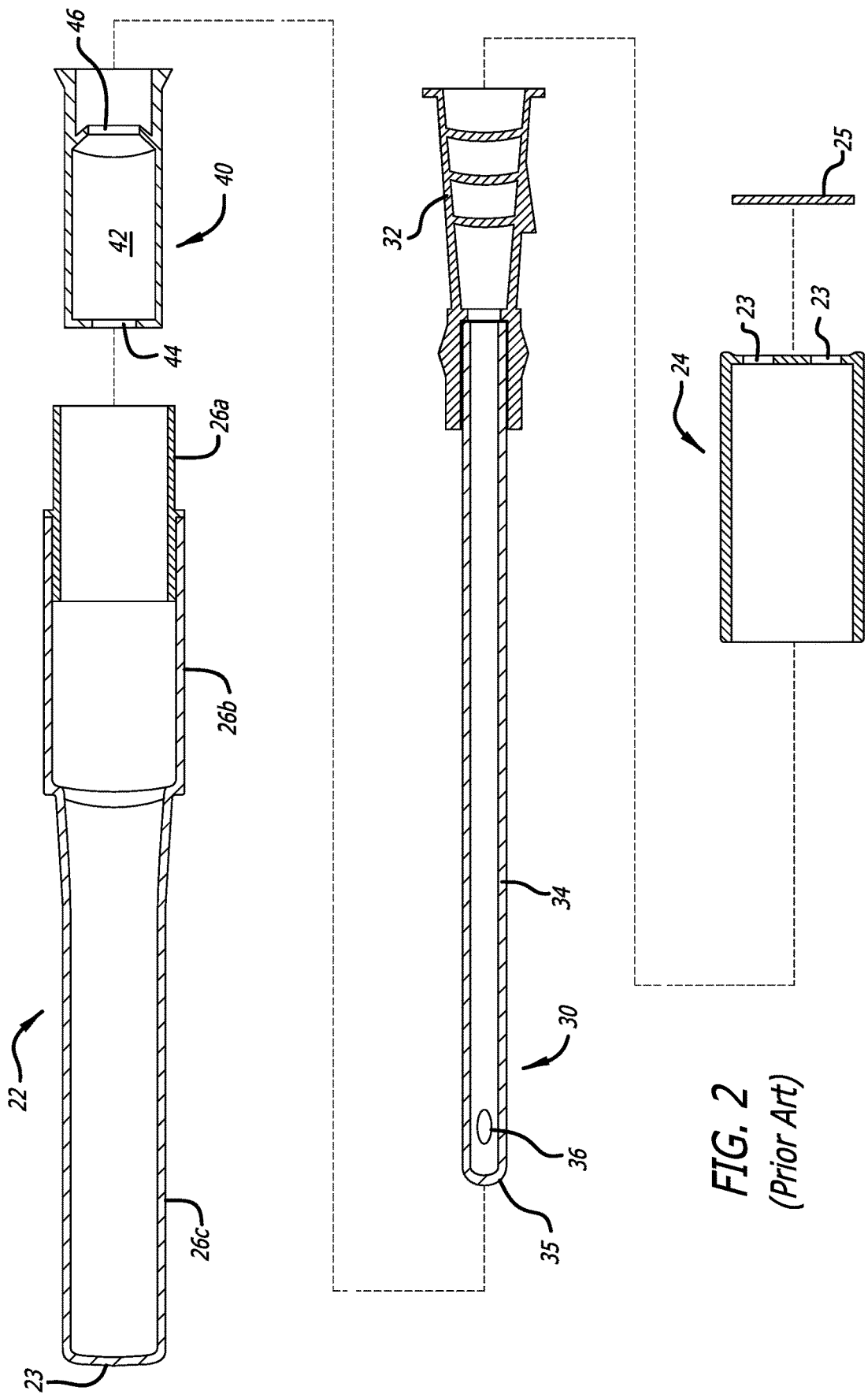
FIG. 2 is an exploded view of the components thereof.

The main body 22 is desirably an assembly of a long distal portion with a shorter tubular connector (that forms the third part 26a) bonded thereto for ease of molding (see FIG. 2). The rigid cap 24 can be attached to the connector 26a of the main body 22 using various attachment/locking methods, such as a screw thread, a bayonet closure or a clamping arrangement. The cap 24 desirably has a plurality of openings (not shown) to permit the introduction of a sterilizing gas into the catheter package.

As illustrated, the urinary catheter 30 is stored in a sterile condition within the main body 22 with the cap 24 on. At a proximal end thereof, catheter 30 is provided with a catheter outlet 32 having a throughbore, which may be used as an outlet funnel or as a connector to attach the catheter 30 to a collection bag or other collection device. Catheter 30 includes a flexible catheter tube 34 provided with a rounded tip 35 on a distal end and one or more flow openings 36 proximate the tip. The catheter tube 34 has a lumen in fluid communication with the throughbore of the outlet 32. Openings 36 are provided with rounded and or polished edges 38, such that the entry of urinary catheter tube 34 into the urethral tract of a patient is as comfortable as possible for the patient. The first part 26a of the main body receives the cap 24, the second part 26b holds a gel holder 40, and the third part 26c holds the elongated catheter tube 34 of the catheter 30.

The rigid nature of the container 20 and short length of the catheter 30 therein make the sterile package formed by the assembly highly portable and conveniently stored in a purse or even pocket.

The cap 24 contains the proximal outlet 32 of the catheter 30 and may be made of a transparent material, which allows inspection of the outlet 32 (which can, e.g., show size or other indicia, markings, etc.). To facilitate gas sterilization of the components inside the main body 22 with the cap 24 attached, cap 24 is provided with one or more openings 23 that are sealed off with filter element 25, e.g. in the form of a paper or other porous element. For instance, a spun bonded polyolefin material (sold under the tradename Tyvek) may be used which can be heat welded to the cap 24 to provide a seal. After assembling the main body 22 (including bonding the connector 26a), gel container 40, catheter 30 and cap 24, the internal elements of the package are sterilized by introducing a gas such as ethylene oxide through the one or more openings 23 in cap 24.

The dimensions of container 20 (or more specifically, the internal dimensions of main body 22 and cap 24) are adapted to allow storage of the entire catheter 30 (which may have varying dimensions). A length of the container 20 desirably corresponds closely to the length of catheter 30, and is preferably slightly greater than the length of catheter 30 so that the package closely surrounds the entire catheter 30. In accordance with embodiments, catheter 30 can have a length in a range of between about 10-15 cm, which makes catheter 30 especially suited for use with female patients.

The gel holder 40 is provided and positioned in second part 26b of main body 22. Gel holder 40 is illustrated as a single generally tubular element provided with a cavity 42 in which an amount of a gel-like lubricant agent G is stored. As seen in FIG. 2, gel holder 40 includes distal opening 44 at a distal end thereof, and proximal opening 46 at a proximal end thereof. Distal opening 44 has a diameter corresponding generally to outer diameter of catheter tube 34, while proximal opening 46 has a diameter slightly greater than the outer diameter of catheter tube 34. The distal and proximal openings 44, 46 are aligned with each other along a longitudinal centerline 50 extending between the distal and proximal ends of the gel holder 40. When taking or otherwise removing catheter 30 in a proximal direction out of the package (to the right in FIG. 1), a layer of the gel-like lubricant extrudes through proximal opening 46 and is deposited on the outside surface of the catheter for use.

Gel Container Inserts

Figure 3:
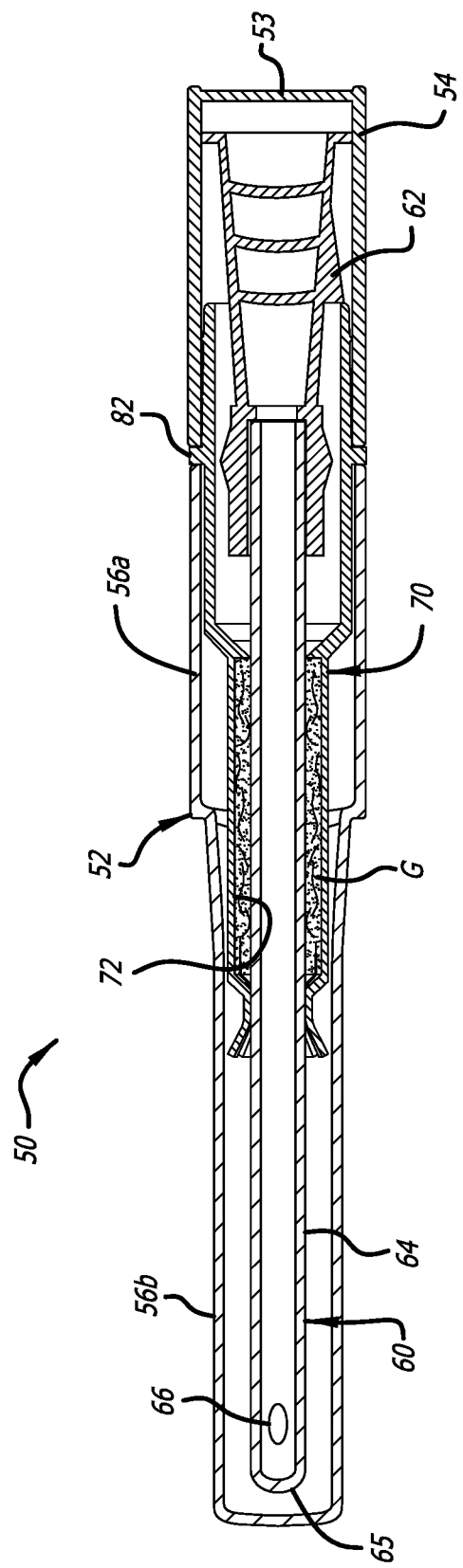
FIG. 3 is a longitudinal sectional view through a sterile container for an intermittent urinary catheter of the present application.

FIG. 3 is a longitudinal sectional view through a sterile container 50 for an intermittent urinary catheter of the present application, FIG. 4 is an exploded view of the components thereof, and FIGS. 5A-5E are perspective and other views of a gel holder used in the sterile container. The sterile container 50 is utilized in much the same manner as the container 20 described above, but is constructed and assembled in a more straightforward and less costly manner.

The sterile catheter container 50 includes a pen-like, rigid and generally hollow tubular main body 52 which is closed off at a distal end, and which can be closed off at a proximal, open end using cap 54. The rigid cap 54 can be attached to the main body 52 using various attachment/locking methods, such as a screw thread, a bayonet closure or a clamping arrangement. The end 53 of the cap 54 is solid and closes off the proximal open end of the main body 52 to prevent the introduction of air or other contaminants into the hollow interior of the catheter package. Sterilization prior to shipping is accomplished using gamma rays or an electron-beam. Preferably, the main body 52 and cap 54 are formed of a rigid material such as polypropylene for recycling purposes.

The cross-sectional view of main body 52 shows a proximal first section 56a and a distal second section 56b. Preferably, proximal section 56a has a first inner diameter which is greater than a second inner diameter of distal section 56b. Both sections 56a, 56b are generally tubular to as to define cylindrical hollow interiors.

As illustrated, with the cap 54 on, a urinary catheter 60 is stored in a sterile condition within the main body 52. At a proximal end thereof, catheter 60 is provided with a catheter outlet 62, which may be used as an outlet funnel or as a connector to attach the catheter 60 to a collection bag or other collection device. Catheter 60 includes a flexible catheter tube 64 provided with a rounded tip 65 on a distal end and one or more flow openings 66 proximate the tip. Openings 66 are provided with rounded and or polished edges, such that the entry of urinary catheter tube 64 into the urethral tract of a patient is as comfortable as possible for the patient.

The rigid nature of the container 50 and short length of the catheter 60 therein make the sterile package formed by the assembly highly portable and conveniently stored in a purse or even pocket, as it resembles a standard item of cosmetics such as eyeliner. Urinary catheters come in different lengths depending on the user: There are conventionally three lengths: female (10-26 cm), standard for men (40-45 cm) and pediatric (30-31 cm). The containers and short catheters disclosed herein are desirably for females and are between 10-26 cm in length, while compact versions that may be housed in a small purse-sized package are between about 10-15 cm long.

An elongated gel holder 70 is provided and positioned in the main body 52. The tube 64 of the urinary catheter 60 extends through the entire gel holder 70 such that the distal tip 65 is within the hollow interior of the main body 52.

Gel holder 70 is illustrated as a single generally tubular molded polymer element provided with a distal inner cavity 72 in which an amount of a gel-like lubricant agent is stored. As seen in FIG. 4, gel holder 70 includes distal opening 74 at a distal end thereof, and proximal opening 76 at a proximal end thereof. Distal opening 74 has a diameter corresponding generally to an outer diameter of catheter tube 64, while proximal opening 76 has a diameter slightly greater than the outer diameter of catheter tube 64. The distal and proximal openings 74, 76 are aligned with each other along a longitudinal centerline 50 extending between the distal and proximal ends of the gel holder 70. When the cap 54 is removed the proximal outlet 62 projects out of the gel holder 70 so as to be graspable. When removing catheter 60 in a proximal direction out of the package (to the right in FIG. 3), a layer of the gel-like lubricant extrudes through proximal opening 76 and is deposited on the outside surface of the catheter tube 64 for use.

As seen best in FIGS. 5A-5E, the gel holder 70 comprises three generally tubular sections: a proximal section 80a, a middle section 80b, and a distal section 80c. The inner cavity 72 is formed exclusively within the distal section 80c. The proximal and middle sections 80a, 80b are generally coextensive and of the same diameter, and are delineated by an outer circumferential rib 82. The distal section 80c is of a smaller diameter than the proximal and middle sections 80a, 80b, and separated therefrom by a tapered shoulder 83.

As seen in FIG. 3, the gel holder 70 inserts into the open proximal end of the rigid main body 52 such that the smaller diameter distal section 80c reaches a short distance into the distal section 56b of the main body 52. The middle section 80b has an outer diameter similar to an inner diameter of the proximal section 56a of the main body 52, while the outer circumferential rib 82 is sized the same as the proximal section 56a so as to provide a stop preventing further advancement of the gel holder 70 into the container main body 52. The proximal section 80a extends out of the main body 52 and provides a tubular receiver for the cap 54, as will be described. During assembly, the gel holder 70 may be secured in this partially inserted position using adhesives, for example, between the exterior of the middle section 80b and the interior of the proximal section 56a of the main body 52.

Figure 5A:
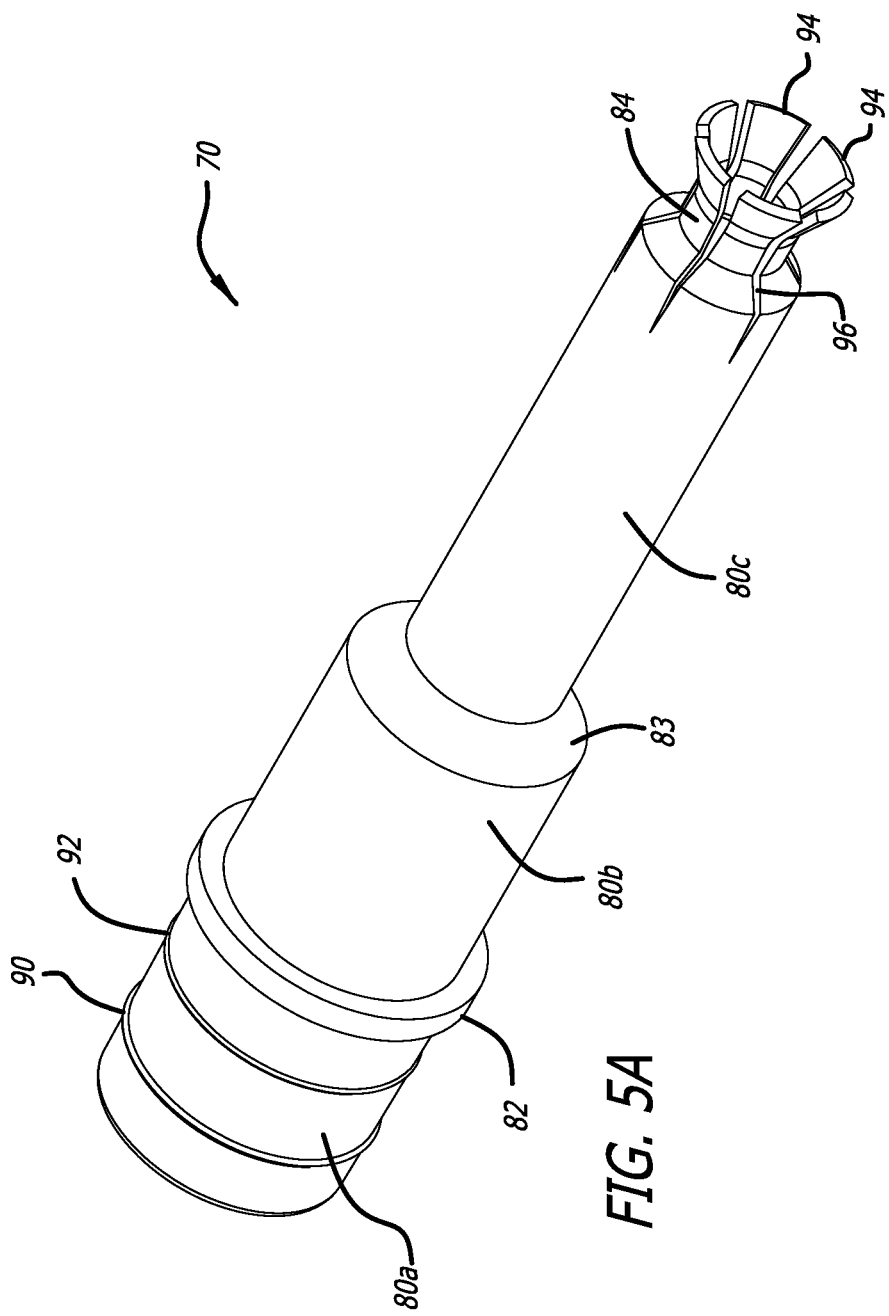
FIG. 5A is a perspective view of a gel holder used in the sterile container of FIG. 3, and FIGS. 5B-5E are sectional and interviews thereof.
Figure 5B:
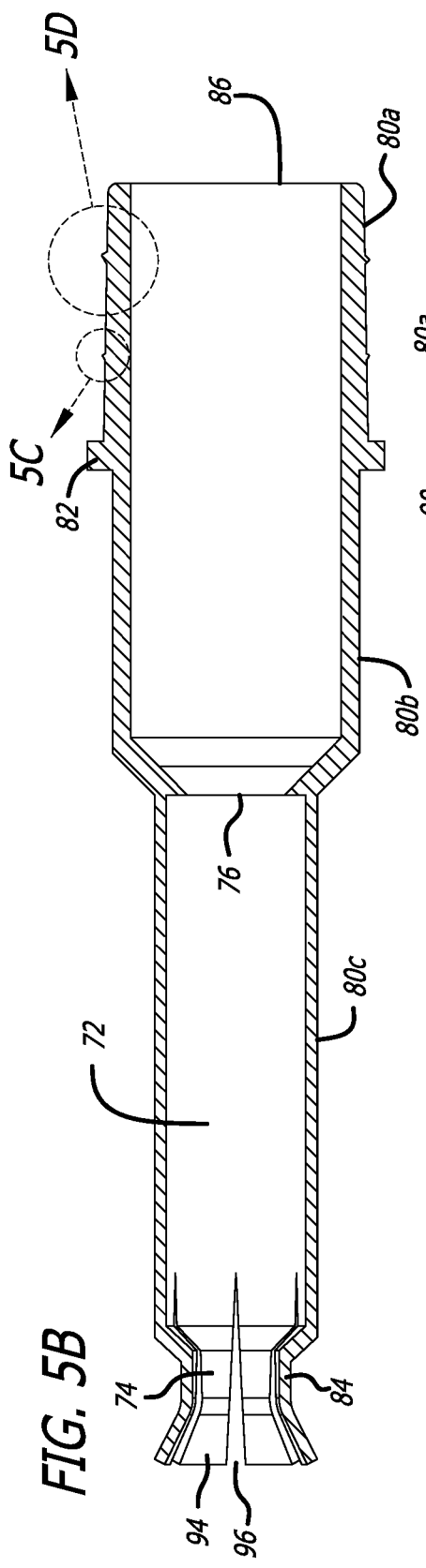
Figure 5C:
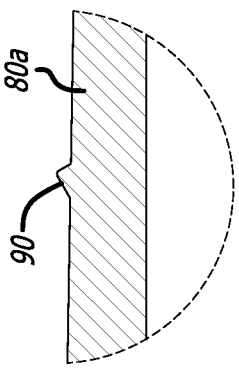
Figure 5D:
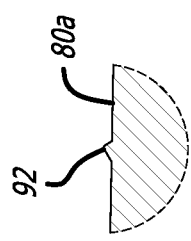
Figure 5E:
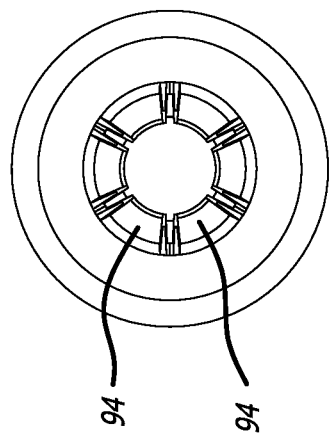

Namely, the proximal section 80a features two circumferential ribs 90, 92, as seen in FIGS. 5A-5D. The nominal outer diameter proximal section 80a is approximately the same as an inner luminal diameter of the tubular portion of the cap 54, while the ribs 90, 92 are larger and interfere with the cap so as to retain and seal it on the proximal section. As seen in the enlargements of FIGS. 5C and 5D, the ribs 90, 92 are slightly different, with the proximal rib 90 being larger, and the distal rib 92 being slightly smaller, though both are asymmetric in cross-section. In particular, the ribs 90, 92 have a steeper proximal face than a distal face, which helps to facilitate removal of the cap 54 when desired. The less steep distal face gives more support to the proximal face during cap assembly to prevent the rib from rolling. The ribs 90, 92 needs to "shear" at the apex to create an airtight seal between cap and body. The proximal rib is sized larger due to the draft (taper) that narrows toward the proximal opening 86 needed to mold the proximal section 80a. The size difference keeps the top of the ribs at the same plane to meet the cap which has an inner lumen molded with no draft (cylindrical).

The cap 54 surrounds the proximal outlet 62 of the catheter 60 and may be made of a transparent material, which allows inspection of the outlet 62 (which can, e.g., show size or other indicia, markings, etc.). To prevent contamination of the components inside the main body 52 with the cap 54 attached, cap 54 is solid with no openings, in contrast to the Twist catheter which has a porous cap. After assembling main body 52, gel container 70, catheter 60 and cap 54, and adding gel to the gel container 70, the internal elements of the package are sterilized by exposure to gamma rays or an electron-beam.

The dimensions of container 50 (or more specifically, the internal dimensions of main body 52 and cap 54) are adapted to allow storage of the entire catheter 60 (which may have varying dimensions). A length of the container 50 desirably corresponds closely to the length of catheter 60, and is preferably slightly greater than the length of catheter 60 so that the package closely surrounds the entire catheter 60. In accordance with embodiments, catheter 60 can have a length in a range of between about 10-15 cm, which makes catheter 60 especially suited for use with female patients. The entire container 50 preferably has a length of no more than 1-2 cm longer than the catheter 60. So, a 10 cm long catheter would be packaged in a container 50 of between 11-12 cm, and a 15 cm long catheter would be packaged in a container 50 of between 16-17 cm.

As mentioned, inner cavity 72 of gel holder 70 includes distal opening 74 at a distal end thereof, and proximal opening 76 at a proximal end thereof. It should be understood that these openings are at the ends of the distal section 80c within which is defined the inner cavity 72.

The overall gel holder 70 has a distal end 84 and a proximal end 86. As seen in FIG. 5A, the distal end 84 is defined by a plurality of cantilevered fingers 94 separated by longitudinal slots 96. The slots 96 commence along the distal section 80c and gradually widen toward the distal end of the fingers 94. With reference to the sectional view of FIG. 5B, the distal end 84 formed by the fingers 94 is molded to constrict the distal end of the distal section 80c, then extend a short linear distance within which is defined the distal opening 74, before flaring outward to the distal end of the fingers 94. As stated, the distal opening 74 has approximately the same diameter as the outer diameter of the catheter tube 64 and as such makes surrounding contact therewith to hold the gel within the inner cavity 72. The cantilevered fingers 94 are molded of a flexible polymer which permits introduction of the lubricant gel into the cavity 72 by inserting a syringe or other such implement between the catheter tube 64 and fingers 94, which flex outward.

By comparing the cross-sections of FIGS. 1 and 3 and respective exploded views of FIGS. 2 and 4, certain distinct advantages between the containers 20, 50 are apparent. First of all, aside from the catheter 60 itself, there are only three molded components in the sterile container 50 as compared with four components with the prior art container 20. Similarly, the gel container 40 of the prior art must be forced into the cavity in the middle part 26b and then filled with gel through the open end of the main body 22 before the catheter 30 is inserted, a dual-action operation that is somewhat exacting and thus time-consuming and expensive. Conversely, the catheter 60 of the present container 20 is first inserted through the gel container 70, and then gel is inserted past the flexible fingers 94 and into the inner cavity 72. This gel-filled assembly is then directly inserted into the rigid main body 52 until the circumferential rib 82 contacts the rear end of the proximal section 56*a*. Finally, the catheter package described herein is completed by adding the cap 54, while the prior art cap 24 must first be combined with the filter element 25, adding another manufacturing step.

In short, the manufacturing advantages of the present container 50 are significant and reduce the costs in a meaningful way in a product whose profit margins are relatively thin to start with. Profit margins are low due to federal government oversight on reimbursement levels for this product. Once the government sets a reimbursement rate, other insurers quickly set their rates at 60-85% of the govt rate. The improved design also lends itself to automation which the prior art design does not mainly due to the difficulty of filling gel once the gel holder is assembled to the tube. This reduces manufacturing costs, which although slight, has a disproportionate impact on profit.

Figure 6:
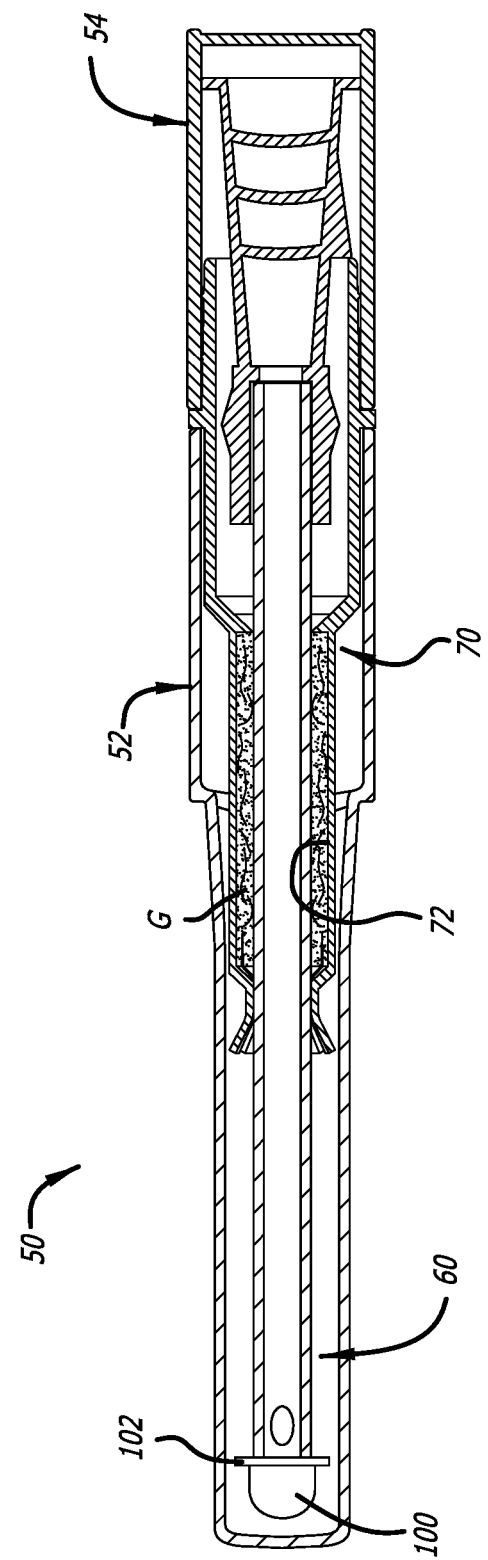
FIG. 6 is a longitudinal sectional view through a sterile container for an intermittent urinary catheter similar to that shown in FIG. 3, and with the addition of a gel cap for the catheter tube.

FIG. 6 is a longitudinal sectional view through the sterile container 50 for an intermittent urinary catheter with the addition of a gel cap 100 for the catheter 60, and FIGS. 7A-7D show several steps in removal of the catheter tube from within the rigid container 50, with the end result being complete coverage of the catheter tube with lubricant gel G.

In some cases, removal of the catheter 60 from within the container 50 may not completely cover the distal tip of the catheter tube with gel, resulting in a dry tip which may hinder introduction into the urethra. Consequently, the gel cap 100 is provided. The gel cap 100 includes a hemispherical cup filled with gel that fits over the distal tip of the catheter 60. The gel cap 100 may be added after the catheter 60 is assembled with the gel container 70 as described above, and preferably after filling the inner cavity 72 with gel. The gel cap 100 remains stuck on the end of the catheter 60 during shipping and handling of the container 50 by the customer by virtue of the viscosity of the gel inside.

FIGS. 7A-7D show several steps in removal of the catheter 60 from the container 50. As the catheter tube 64 slides out of the gel container 70, gel G coats the outer surface thereof. At the position shown in FIG. 7B, a circular flange 102 on a proximal end of the gel cap 100 contacts the distal end 84 of the gel container 70 within the main body 52. Further withdrawal of the catheter 60 causes the gel cap 100 to fall off the end of the tube 64, as seen in FIG. 7C. Gel G coats the end of the tube 64. Finally, in FIG. 7D, after complete withdrawal, the distal end catheter tube 64 is totally coated with gel G on the distal end and for most of its length. This facilitates introduction into the urethra, and eliminates the occasional problem of a dry tip.

Figure 8:
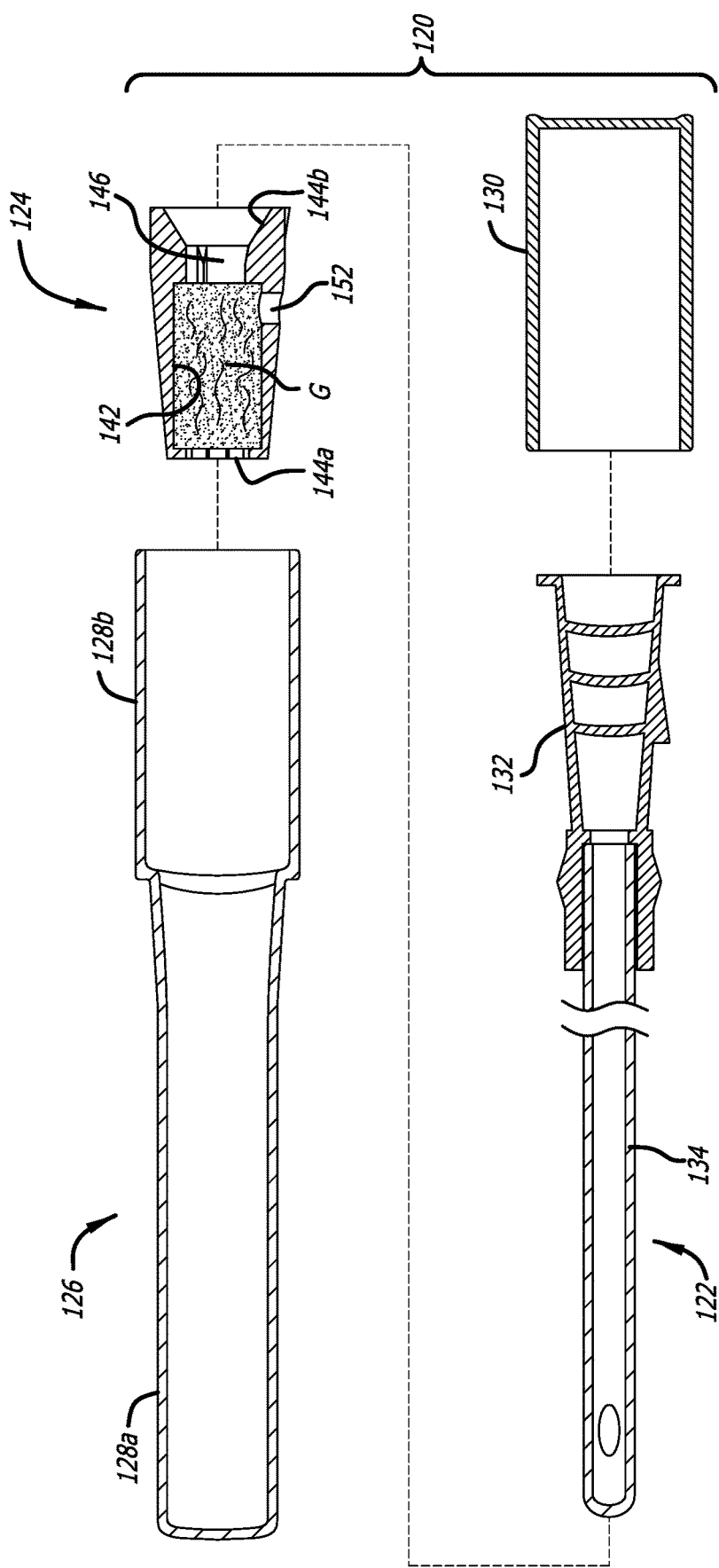
FIG. 8 is an exploded longitudinal sectional view through an alternative sterile container for an intermittent urinary catheter in which a gel holder is inserted therein.

FIG. 8 is an exploded longitudinal sectional view through an alternative sterile container 120 for an intermittent urinary catheter 122 in which a gel holder 124 is inserted therein. As with earlier versions, the sterile container 120 comprises a generally tubular rigid main body 126 having an elongated, closed distal end 128*a* and a slightly larger diameter, open proximal end 128*b*. An end cap 130 is sized to engage and enclose the open proximal end 128*b*, creating a sterile interior cavity. The urinary catheter 122 once again has a proximal outlet or funnel 132 attached to a distal tube 134 for insertion in the urethra, the tube having at least one eyelet near a distal end for urine ingress. As will be described, during assembly, the tube 134 of the catheter 122 is sized to pass through the gel holder 124 positioned within the proximal end 128*b* and into the cavity within the distal end 128*a*. The packaged and sterile container 120 and catheter 122 thus forms an assembly much like that shown in FIG. 3, with corresponding exterior dimensions as described above. Namely, the size of the main body 126 is preferably relatively short, such as between 10-15 cm.

FIG. 9 is a perspective view of the gel holder 124 for the urinary catheter of FIG. 8, and FIGS. 9A-9C are orthogonal views thereof. The gel holder 124 has a generally tubular body defined by a distal portion 136 having a conical exterior in series with a proximal portion 138 with a cylindrical exterior and interrupted by regularly-spaced spiral fins 140. In a preferred embodiment, the gel holder 124 is molded from an elastomer, such as silicone, and the spiral fins 140 are thus flexible, though the gel holder may also be polypropylene for recycling purposes. As seen in the end views of FIGS. 9B and 9C, the fins 140 extend radially outward from the rest of the tubular body of the gel holder 124.

The outer diameter of the cylindrical proximal portion 138 is sized slightly smaller than the inner diameter of the proximal end 128*b* of the main body 126, while the outer diameter of a circle of revolution defined by the fins 140 is greater than the inner diameter of the proximal end. Consequently, an interference fit is created between the flexible fins 140 and the interior cavity of the proximal end 128*b*, which nominally secures the gel holder 124 within the main body 126, without requiring significant force to couple the two pieces together.

As seen by the cross-section of FIG. 8, the gel holder 124 defines a large inner gel cavity 142 adjacent a distal opening 144*a*. A proximal opening 144*b* has a conical configuration and gradually tapers inward to an inner through bore 146 that opens to the gel cavity 142. The tapered opening 144*b* facilitates a user returning the catheter back into the package after use for eventual disposal. As seen in FIG. 9B, the distal opening 144*a* is formed by an inwardly-directed flange 148 defining a scalloped inner edge. The inner through bore 146 features a series of regularly-spaced inwardly-directed ribs 150—in the illustrated embodiment there are three triangular ribs. The gel holder 124 further includes a side port 152 that extends through the wall of the distal portion 136 and opens to the gel cavity 142.

Assembly of the sterile catheter container 120 and catheter 122 commences with filling of the gel cavity 142 with gel G through the side port 152. Before or after filling the gel cavity 142 with gel G, the tube 134 of the catheter 122 is inserted into the proximal opening 144*b*, and from there all the way longitudinally through the gel holder 124. The tapered shape of the proximal opening 144*b* helps in guiding the catheter tube 134 into the gel holder 124. The catheter tube 134 extends distally beyond the gel holder 124 and the assembly is then inserted into the open proximal end 128*b* of the main body 126 until the gel holder 124 is fully within the main body; with the outwardly-directed fins 140 providing a nominal interference fit therebetween. The inwardly-directed ribs 150 define a circle of revolution which is approximately the same as the exterior diameter of the tube 134. Likewise, the innermost points of the scalloped inner edge of the distal flange 148 define a circle of revolution that is about the same as the diameter of the tube 134. Consequently, the tube 134 of the catheter 122 is aligned by the gel holder 124 along the longitudinal axis of the main body 126. A portion of the proximal funnel 132 remains sticking out of the main body 126 for ease of grasping, and the cap 130 is then engaged around the proximal end 128*b* to enclose the sterile package.

When a user seeks to utilize the urinary catheter 122, they simply remove the cap 130 and pull the catheter from within the main body 126 by grasping the proximal funnel 132. As the catheter tube 134 withdraws through the gel holder 124, gel G coats the exterior thereof so that the tube may be easily inserted into the urethra. Both the scalloped distal flange 148 and the inwardly directed ribs 150 in the inner through bore 146 form interrupted annular spaces around the catheter tube 134 which permit application of a thin layer of gel G to the tube, but act as wipers of a sort to avoid excess gel applications.

Figure 10:
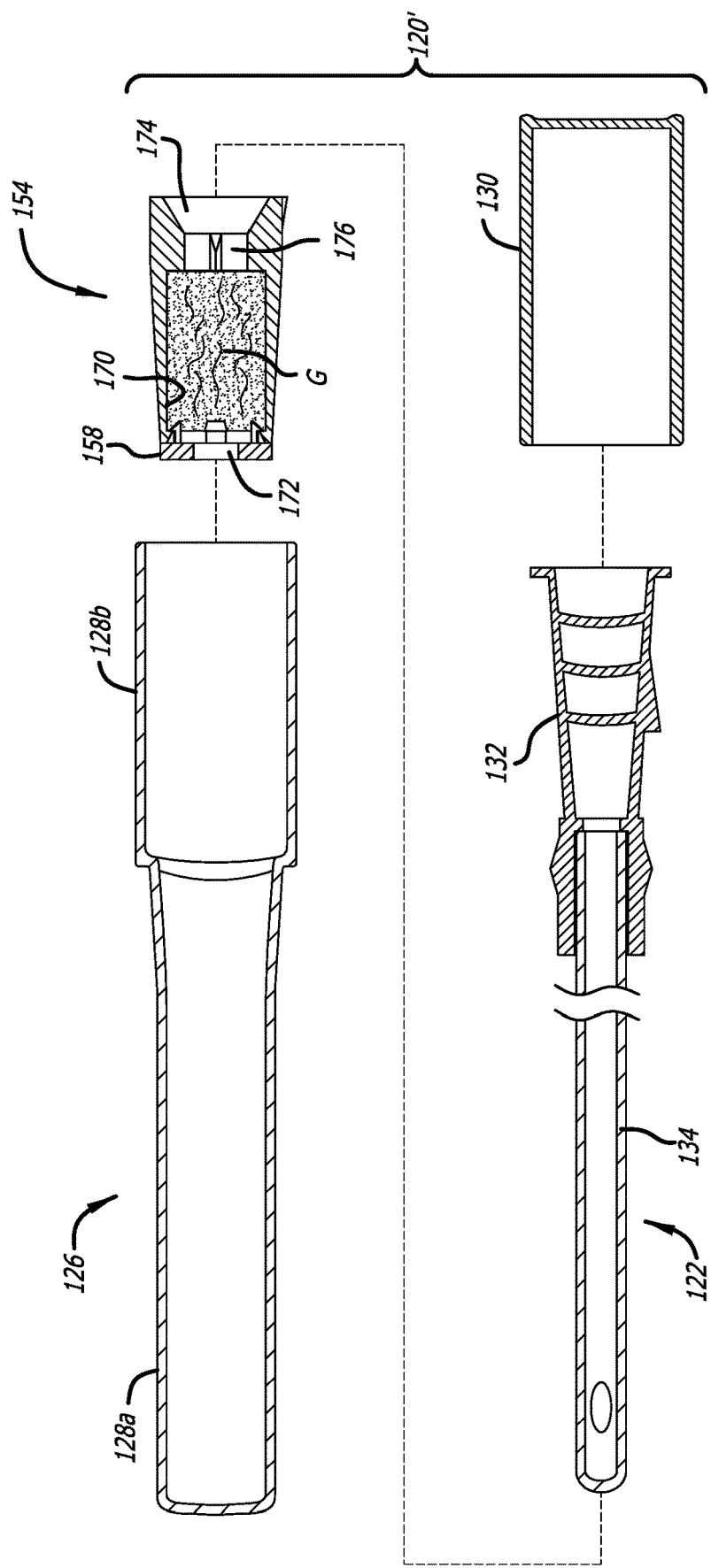
FIG. 10 is an exploded longitudinal sectional view through a further alternative sterile container for an intermittent urinary catheter in which a gel holder is inserted therein.

FIG. 10 is an exploded longitudinal sectional view through a further sterile container 120' for an intermittent urinary catheter in which an alternative gel holder 154 is inserted therein. The sterile container 120' is substantially the same as the sterile container 120 described above, and thus like parts will be given like element numbers. Namely, the sterile container 120 comprises a generally tubular rigid main body 126 having an elongated, closed distal end 128a and a slightly larger diameter, open proximal end 128b. An end cap 130 is sized to engage and enclose the open proximal end 128b, creating a sterile interior cavity. The urinary catheter 122 has a proximal outlet or funnel 132 attached to a distal tube 134 for insertion in the urethra, the tube having at least one eyelet near a distal end for urine ingress. During assembly, the tube 134 of the catheter 122 is sized to pass through the gel holder 154 positioned within the proximal end 128a and into the cavity within the distal end 128a.

Figure 11:
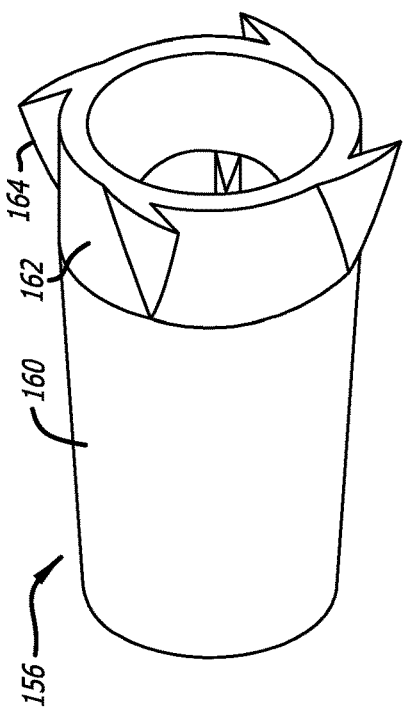
FIG. 11 is a perspective view of a tubular component of the gel holder for the urinary catheter of FIG. 10, and FIGS. 11A at 11B are orthogonal views thereof.
Figure 11B:
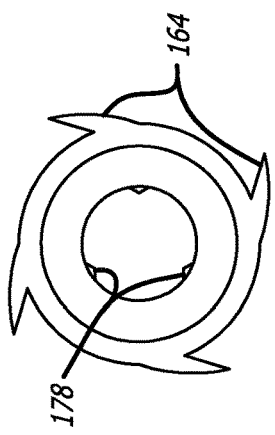
Figure 11A:
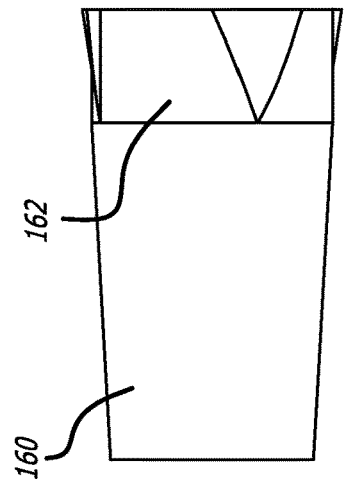
Figure 12:
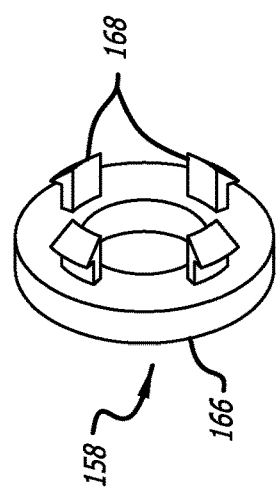
FIG. 12 is a perspective view of a sterile end cap of the gel holder for the urinary catheter of FIG. 10, and FIGS. 12A at 12B are orthogonal views thereof.
Figure 12B:
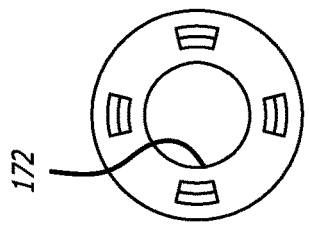
Figure 12A:
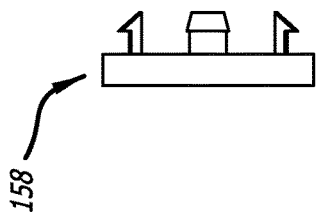

FIG. 11 is a perspective view of a tubular component of the gel holder 154 for the urinary catheter of FIG. 10, and FIGS. 11A at 11B are orthogonal views thereof. The gel holder 154 in this embodiment is an assembly of two components-a tubular main body 156 and a distal end cap 158. The tubular main body 156 is much like the main portion of the gel holder 124 described above, and has a distal portion 160 having a conical exterior and a proximal portion 162 with outwardly-directed fins 164. Once again, the main body 156 is preferably molded of an elastomer or PP and the flexible fins 164 are sized to create an interference fit within the proximal end 128b of the rigid main body 126.

The distal end cap 158 has an annular disk portion 166 and a plurality of teeth 168 extending longitudinally from a proximal face thereof. As seen in FIG. 10, the endcap 158 couples to a distal end of the main body 156, with the teeth 168 projecting a short way into a gel cavity 170 where outwardly directed projections on the teeth engage and inwardly-directed flange at the distal end of the main body. Both the main body 156 and endcap 158 are molded of an elastomer such that the teeth 168 may easily flex inward to pass beyond the end flange. Forming the gel container 154 as an assembly of two components 156, 158 simplifies the molds needed to create the shape of the inner gel cavity 170.

The distal end cap 158 further has an inner opening 172 which defines a through bore for the catheter tube 134. The inner opening 172 may be sized about the same as the outer diameter of the tube 134 to seal against and prevent the gel from migrating past the tube into the closed distal end 128a. The main body 156 further includes a proximal opening 174 having a conical configuration that gradually tapers inward to an inner through bore 176 opening to the gel cavity 170. Again, this taper facilitates a user returning the catheter back into the package after use. Axial ribs 178 as seen in FIG. 11B may be provided to create a small annular space between the through bore 176 and the catheter tube 134 which helps regulate application of a moderate amount of lubricating gel.

To assemble the sterile catheter container 120' and catheter 122, the gel cavity 170 is filled with gel G through the central opening 172 of the distal end cap 158. Before or after filling the gel cavity 170 with gel G, the tube 134 of the catheter 122 is inserted into the proximal opening 174, and from there all the way longitudinally through the gel holder 154. The catheter tube 134 extends into the cavity within the distal end 128a of the main body 126 until the fins 164 of the gel holder 156 contact the inner wall of the proximal end 128b. The tube 134 of the catheter 122 is again aligned by the gel holder 156 along the longitudinal axis of the main body 126. A portion of the proximal funnel 132 remains sticking out of the main body 126 for ease of grasping, and the cap 130 is then engaged around the proximal end 128b to enclose the sterile package.

Folding Gel Containers

Another way to pre-assemble urinary catheters within sterile containers and ensure adequate gel application is to couple a foldable gel holder onto the catheter itself. By providing a folding gel holder, gel may be easily applied to the exterior of the catheter, whereupon the gel holder is folded into a compact configuration for insertion into a rigid outer body. FIG. 13A is a side view showing a pre-assembly of a urinary catheter 180 with a foldable gel holder 182 shown in FIGS. 14A-14C, and FIG. 13B is a side view of the assembly with the gel holder being inserted into a rigid main body 184 of a sterile container. Although not shown, the rigid main body 184 may be similar in size and configuration to those described above, and may be closed off by an endcap (not shown).

Figure 14B:
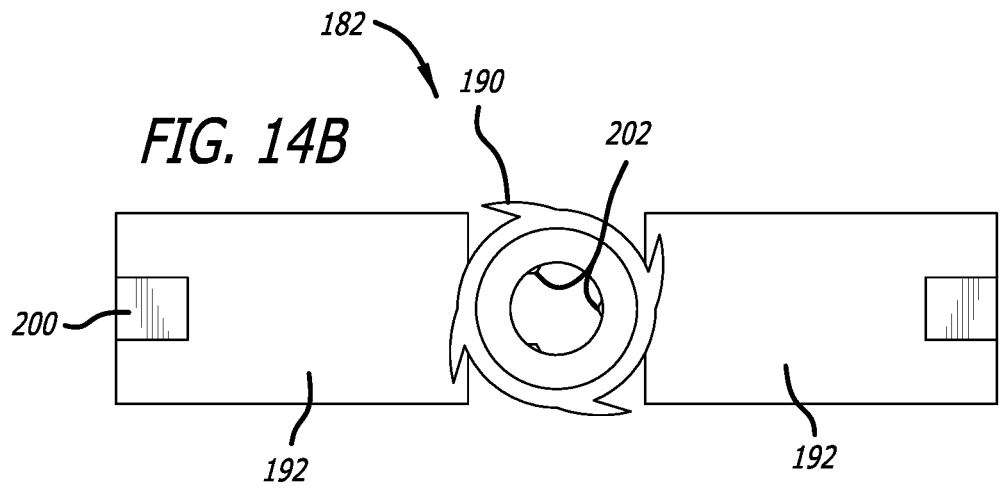
FIGS. 14A-14C are front elevational and top and bottom plan views, respectively, of the foldable gel holder of FIGS. 13A and 13B.
Figure 14A:
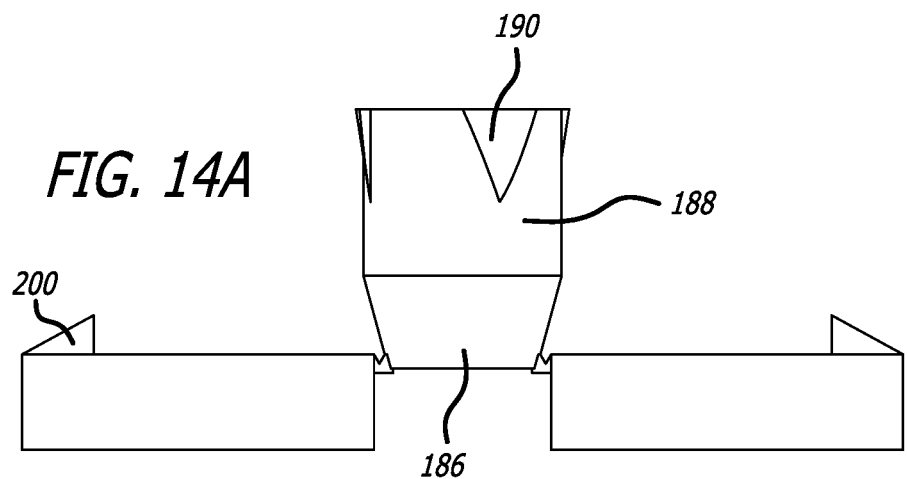
Figure 14C:
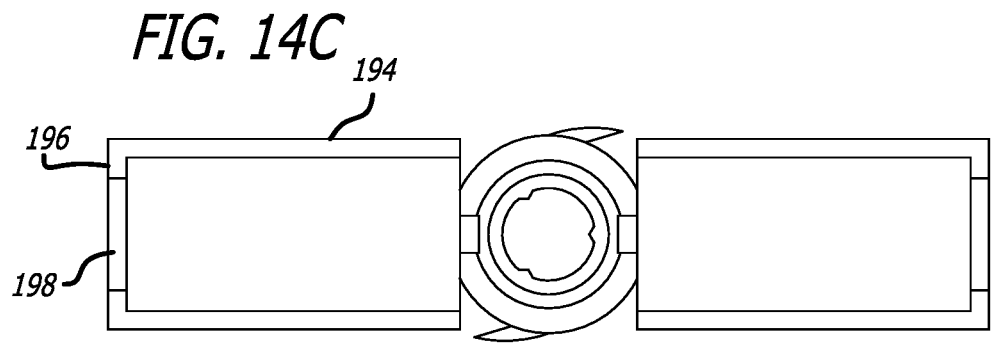

With reference to FIGS. 14A-14C the foldable gel holder 182 comprises a generally tubular body defined by a distal portion 186 having a conical exterior in series with a proximal portion 188 with a cylindrical exterior and interrupted by regularly-spaced spiral fins 190. A pair of folding arms 192 are pivotally connected to a distal end of the distal portion 186, such as with living hinges. The arms 192 may be pivoted open as seen in FIG. 13A to be generally perpendicular to the longitudinal axis of the gel holder 182, and then pivoted closed as seen in FIG. 13B in line with the longitudinal axis. Each of the arms 192 is formed by a hollow shell 194 having a semi-circular cross-section along a majority of its length and terminating in an end wall 196 having a semi-circular opening 198 form therein. When the two arms 192 are brought together in the closed configuration, as seen in the sectional view of FIG. 13C, a gel cavity is formed within the shells 194 having a distal opening formed by the two juxtaposed semi-circular openings 198.

Each of the arms 192 may also have an outwardly-extending projection or wedge 200 which is sized to engage an inner wall of the rigid main body 184. The wedges 200 along with the outwardly projecting fins 190 thus center and secure the gel holder 182 within the rigid main body 184.

The advantage of having folding arms 182 forming the gel holder 182 is seen by the assembly snapshots of FIGS. 13A and 13B. The catheter 180 is first inserted through a central through bore of the tubular body of the gel holder 182 with the arms 192 pivoted open. Gel G is then applied around a short portion of the tube of the catheter 180 as shown. Once the arms 192 are pivoted to the closed position, as seen in FIG. 13B, the assembly may be inserted within the rigid main body 184. The flexible or soft wedges 200 and fins 190 engage the inside of the rigid main body 184 to hold the gel container 182 centrally aligned and in place. Finally, a closure or cap as described above is secured around the proximal end of the rigid main body 184, thus maintaining sterility within the package. These steps may easily be automated for manufacturing savings.

When the cap is pulled off, the catheter 180 may be withdrawn from the container with gel G being applied to the exterior of the catheter tube. Inwardly directed ribs 202 as seen in FIG. 14B may be provided within the through bore of the tubular portion of the gel holder 182 to ensure an even and non-excessive application of gel G on the catheter tube.

Figure 15A:
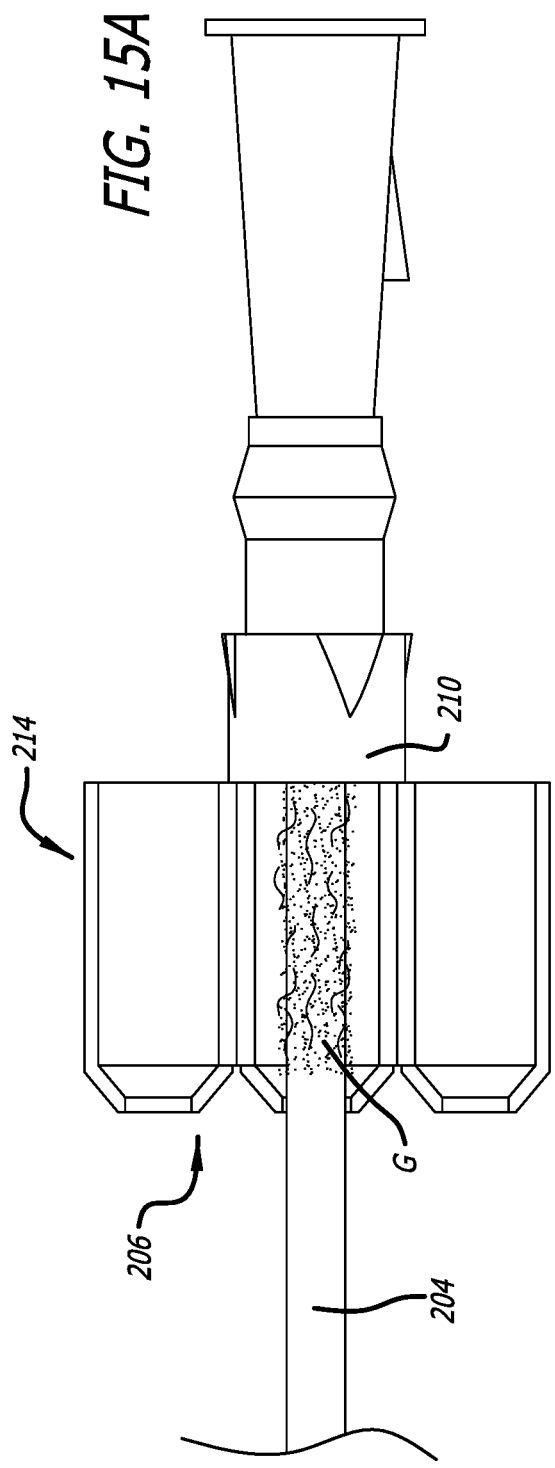
FIG. 15A is a side view showing a pre-assembly of a urinary catheter with an alternative foldable gel holder.
Figure 15B:
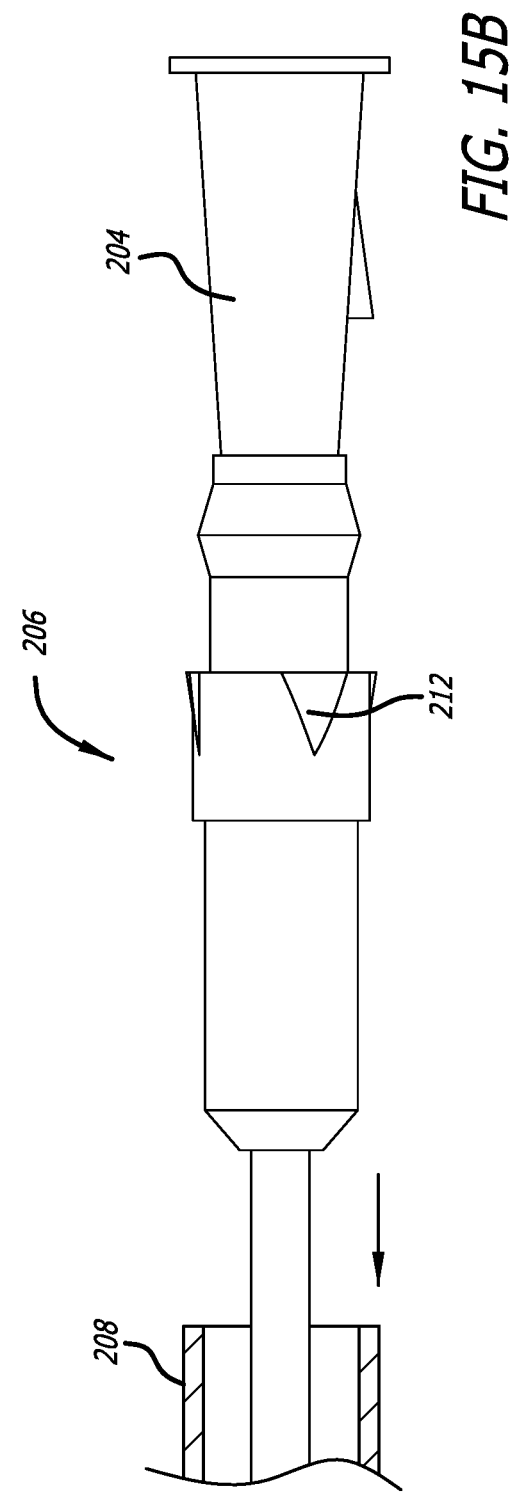
FIG. 15B is a side view of an assembly of the urinary catheter with gel holder being inserted into a rigid main body of a sterile container.

FIG. 15A is a side view showing a pre-assembly of a urinary catheter 204 with an alternative foldable gel holder 206, and FIG. 15B is a side view of an assembly of the urinary catheter with gel holder being inserted into a rigid main body 208 of a sterile container. In general, the foldable gel holder 206 functions in a similar manner as the gel holder 182 described above with respect to FIGS. 13A and 13B, with the folding configuration being different.

Specifically, as seen in FIGS. 16A and 16B, of the foldable gel holder 206 comprises a generally tubular proximal portion 210 having outer fins 212. A distal portion comprises a number, in this case three, longitudinally hinged portions 214 which may be opened up as shown, and as seen in FIG. 15A, and then pivoted closed to form a generally cylindrical gel cavity therein. More particularly, each of the hinged portions 214 comprises a hollow shell 216 defining an approximately 120° outer span of the assembled gel holder 206, and each having a planar end wall segment 218.

FIG. 17A is a sectional view through a midportion of the gel holder 206 indicating a folding operation. Folding the hinged portions 214 closed brings the end wall segments 218 together to define a distal opening 220, as seen in FIG. 17B.

FIG. 15A shows a first step in an assembly procedure wherein the catheter 204 is inserted through a central through bore of the tubular body 210 of the gel holder 206 with the hinged portions 214 pivoted open. Gel G is then applied around a short portion of the tube of the catheter 204 as shown. Once the hinged portions 214 are pivoted to the closed position, as seen in FIG. 15B, the assembly may be inserted within the rigid main body 208. The flexible or soft fins 212 engage the inside of the rigid main body 208 to hold the gel container 206 centrally aligned and in place. Finally, a closure or cap as described above is secured around the proximal end of the rigid main body 208, thus maintaining sterility within the package. Again, these steps may easily be automated to facilitate manufacturing.

When the cap is pulled off, the catheter 204 may be withdrawn from the container with gel G being applied to the exterior of the catheter tube. Inwardly directed ribs 222 as seen in FIG. 16B may be provided within the through bore of the tubular body 210 of the gel holder 206 to ensure an even and non-excessive application of gel G on the catheter tube as it is withdrawn. The ribs 222 also serve to hold the gel holder 206 on the catheter 204 during assembly.

Bulkheads/Divider Walls/Inserts Forming Internal Gel Cavities

A still further way to pre-assemble urinary catheters within sterile containers and ensure adequate gel application is to form internal cavities within the rigid outer body using bulkheads or divider walls that segregate an internal volume in which gel can be inserted. Various solutions are contemplated, and one advantage is a simplification of the molding and/or manufacturing process, thus reducing cost.

The basic idea of using bulkheads or walls to form internal cavities is elimination of a silicone gel holder, which may be expensive to make and difficult to automate assembly. The gel holder would be replaced by 2 walls or bulkheads within the body of the device. The body may be either one piece or 2 (or more) pieces. The advantage of a 2-pc design is that the shorter segments are easier to manufacture and could incorporate one or both of the internal bulkheads thus saving part count. A multi-piece body would be assembled using a welding or bonding technique such as spin-welding, ultrasonic welding, solvent bonding, adhesive bonding etc. Spin-welding is a very fast operation and is easily made part of an automated assembly line.

The distal bulkhead, nearest the tip of the catheter, will be tight fitting to the tube and can be either an inserted component or molded into the body. The distal bulkhead may contain a tight fitting inner ring molded of a softer durometer material to seal the catheter. One concept is that all parts are molded of a polypropylene (PP) material, (PP) blend or polyethylene (PE) that will be a softer durometer than current outer cases. Making all parts of the same material has the advantage of being recyclable after use. A proximal bulkhead is designed to allow for a slight gap between the insert and the catheter tube to allow for the gel to be distributed in a thin layer as the tube is withdrawn. The slight gap is produced by using stand-offs in the proximal bulkhead ID to hold the catheter away from the main ID. These stand-offs also function as an assembly aid to hold the insert on the tube during assembly. This proximal bulkhead will be either a separate insert that is assembled to the tube prior to gel dispensing and final assembly or will be molded into the proximal portion of the body in a 2-pc body design. It should be understood that the terms bulkhead, inserts and divider walls are essentially synonymous in terms of providing an internal barrier extending transversely across the rigid main body that serves to segregate one internal cavity from another. Two internal barriers spaced apart form the gel cavity, and each includes a throughbore for passage of the tube of the urinary catheter.

FIG. 18 is a longitudinal sectional view through a sterile container 228 for a urinary catheter having internal spaced bulkheads defining an inner gel cavity. The sterile container includes a rigid main body 230 molded of PP or PE having a closed distal end opposite an open proximal end that receives a closure or cap 232. The size and shape of the main body 230 is similar to those described above, and is preferably relatively short, between 10-15 cm.

The sterile container 228 is generally hollow along its length for receiving a urinary catheter 234, such as seen in FIG. 19, with two internal walls or bulkheads which segregate the hollow interior into three cavities. More specifically, a distal bulkhead 236 is molded into the inner wall of the main body 230, and is shown in the enlargement of FIG. 18A. The distal bulkhead 236 desirably extends in a circle around the interior of the main body 230 and defines a border between a distal cavity 238a and a middle cavity 238b. A proximal bulkhead 240 comprises a separate, generally tubular piece that is inserted into the hollow space within the main body 230, and which defines a border between the middle cavity 238b and a proximal cavity 238c.

FIG. 19 is a longitudinal sectional view of the sterile container 228 with the urinary catheter 234 stored therein and gel G placed in the middle cavity 238b between the bulkheads 236, 240. The middle cavity 238b thus takes the place of the previously-described gel holders. The inner diameter of the distal bulkhead 236 is approximately the same as the external diameter of the tube of the catheter 234, and thus prevents gel from migrating into the distal cavity 238a.

In the illustrated embodiment, the distal bulkhead 236 is formed by a thin inward circular projection which is tapered to a point and slightly curved in the proximal direction so as to act as a wiper of sorts, but also to facilitate the internal molding process. The main body 230 may be formed of a rigid material such as polypropylene for recycling purposes, and the distal bulkhead 236 is thin enough to be somewhat flexible. It should also be noted that the thickness of the main body 230 may be increased in the distal region surrounding the distal cavity 238a. This is shown by the change in thickness from $t_d$ to $t_p$ in FIG. 18A. The thickness in the distal end varies depending on the diameter of the tube of the catheter 234, whereby thicker walls reduce the orifice defined by the bulkhead 236. For example, catheter tubes for use by females vary between 8-16 French, or between 2.7-5.3 mm. The wall thickness in the distal end of the main body 230 is thus made thicker for smaller catheters.

The proximal bulkhead 240 is formed by a generally tubular solid member having a through bore 242 that is slightly larger than the external diameter of the tube of the catheter 234, and is thus between 2.7-5.3 mm. The inner wall 231 of the main body 230 tapers down in diameter from the open proximal end to a point about one third of the way along its length, such that the bulkhead 240 may be inserted and pressed a short distance into the main body before it gets stuck within the inner wall, as shown. A tapered inlet 243 facilitates introduction of the tube of the catheter 234 into and past the through bore 242. There are a number of ways to shape the external structural features of the bulkhead 240 or the internal structural features of the inner wall 231 of the main body 230 so as to provide friction or interference therebetween and enable insertion of the bulkhead 240 to a predetermined depth within the hollow interior.

Assembly of the sterile container 228 involves first placing the proximal bulkhead 240 onto the tube of the catheter 234. Desirably, the through bore 242 of the bulkhead 240 has inner axial ribs (not shown) which are sized to provide an interference fit around the tube. A predetermined volume of gel G may be easily added to the shaft of the catheter below the proximal bulkhead 240, whereupon the urinary catheter 234 is inserted into the position shown in FIG. 19, and the cap 232 secured on the proximal end for sterility. The gel G is thus constrained within the middle cavity 238b, and is available to cover the distal end of the tube of the catheter 234 when it is withdrawn from the main body 230. The through bore 242 is slightly larger than the tube so that an even, relatively thin layer of gel G is applied along the tube and at the distal tip. Inner axial ribs such as shown above at 222 in FIG. 16B may also be included within the through bore 242 to allow for assembly, center the catheter tube and regulate the amount of gel G applied.

FIG. 20 is an exploded side view of a still further sterile container 244 along with a urinary catheter 246 in a pre-assembled configuration, and FIG. 21 is a longitudinal sectional view through the assembled sterile container and urinary catheter. The container 244 again has internal bulkheads which segregate an inner cavity for insertion of gel, though in contrast to the embodiment of FIG. 19, both the bulkheads are separate pieces and not molded into a rigid main body 248.

In particular, a distal bulkhead 250a is first inserted a predetermined depth into the hollow main body 248. The inner wall of the main body 248 may be tapered such that the bulkhead 250a becomes stuck at a certain point, or an inner rib or other such inward projection may be provided to halt advancement of the bulkhead. Likewise, a proximal bulkhead 250b is inserted into the hollow main body 248 to a depth which creates spacing between the two bulkheads. In one version, both bulkheads 250a, 250b are slightly tapered the facilitate insertion into the lumen of the body 248. It should be understood that external structural features of the bulkheads 250a, 250b and/or internal structural features of an inner wall of the hollow main body 248 are configured so that the bulkheads may be inserted to predetermined spaced-apart depths within the hollow interior.

At this point, gel G may be added into the space between the two bulkheads 250a, 250b and then the catheter 246 may be inserted and a cap secured thereon. However, another assembly method is to couple the proximal bulkhead 250b around the tube of the catheter 246, as seen in FIG. 20, and then simply apply gel G to the exterior of the tube as shown. The subassembly of the catheter 246 and proximal bulkhead 250b can be inserted into the main body 248 and through the distal bulkhead 250a, to result in the assembly of FIG. 21.

Figure 22:
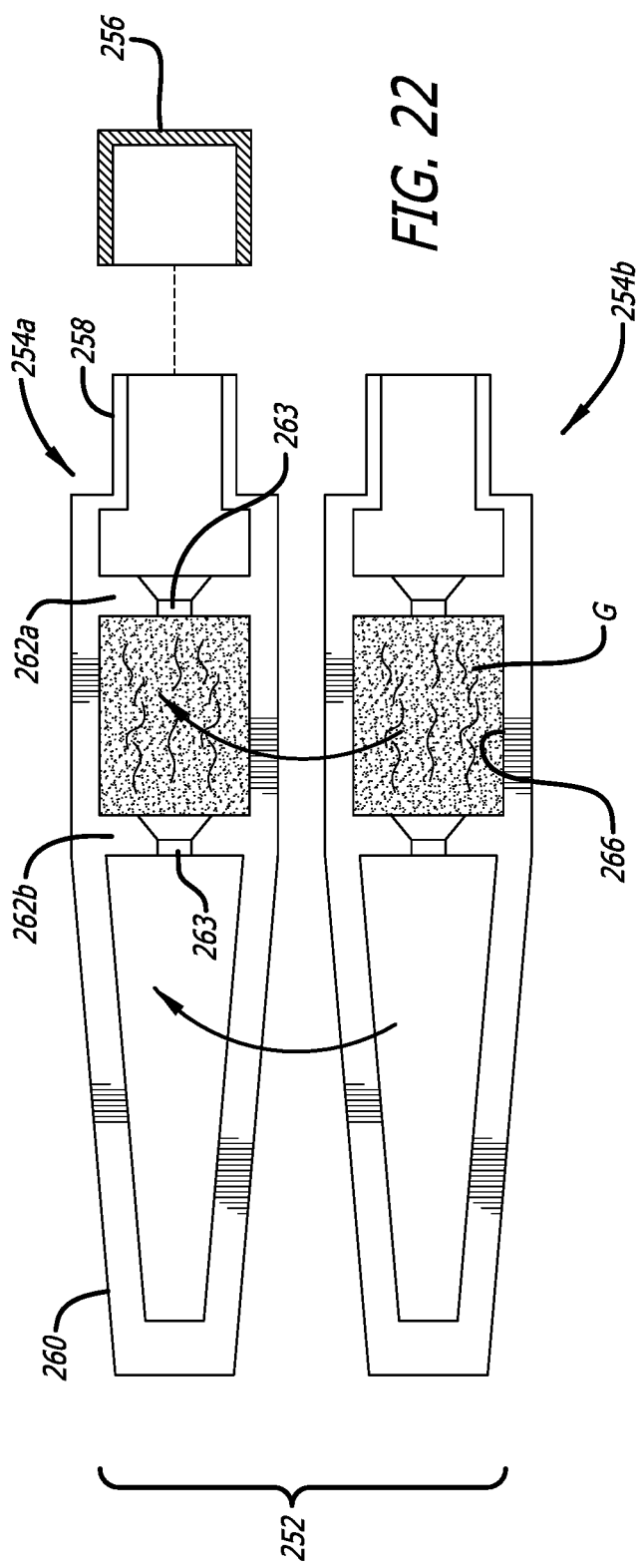
FIG. 22 is a top plan view of components of a further sterile container including two molded halves and a sterile end cap.

FIG. 22 is a top plan view of components of a further sterile container 252 including two identical molded halves 254a, 254b and a sterile end cap 256. Each half is a single molded part in the form of a generally hemi-cylindrical trough with outer walls that extend from a proximal end 258 to a distal end 260. The outer walls define a longitudinal partial cavity and a pair of bulkheads 262a, 262b extend across the cavity perpendicular to the longitudinal axis. Each of the bulkheads 262a, 262b defines a through bore 263 having a tapered inlet opening to the proximal side. These tapers help a user returning the catheter back into the package after use for eventual disposal. The two halves 254a, 254b both have one side lying in a single plane (facing out of the page) and can thus be brought together in a flush manner as indicated by the arrows. The two halves 254a, 254b are sealed together to form the assembled container 252.

Figure 23:
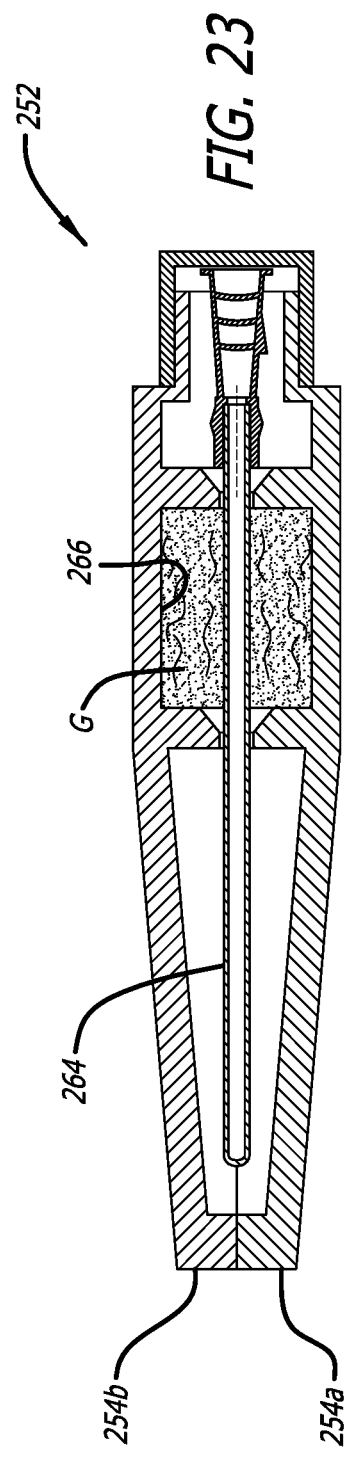
FIG. 23 is a longitudinal sectional view through the sterile container and urinary catheter as assembled.

FIG. 23 is a longitudinal sectional view through the sterile container 252 and a urinary catheter 264 as assembled. The tube of the catheter 264 extends through both of the bulkheads 262a, 262b and into a distal cavity. A middle cavity 266 defined within the hollow interior of the outer walls and between the bulkheads 262a, 262b may be filled with lubricant gel G. A proximal end of the catheter projects slightly out of the proximal end 258 of the container, with the cap 256 applied for sterility.

The lubricant gel G may be injected into the middle cavity 266 within both halves 254a, 254b, and the catheter 264 dropped into one of the halves before the halves are brought together. Desirably, the two halves 254a, 254b are sealed and then pressure tested before adding the cap 256. A hermetic seal between the two halves 254a, 254b may be formed by using a press fit, a sonic weld, a solvent bond, or adhesive. Again, the container 252 is desirably molded of polypropylene so that it may be recycled. In an alternative assembly, the container 252 may be first formed, after which a predetermined volume of gel G is inserted through the proximal bulkhead 262a into the middle cavity 266, and then the catheter 264 is inserted and the cap 256 applied.

FIGS. 24A and 24B are top plan and end elevational views of a clamshell-type of sterile container 270 prior to assembly showing a urinary catheter 272 and gel G placed therein in a pre-assembled configuration. FIGS. 25A and 25B are top plan and end elevational views of the assembled clamshell-type sterile container 270 and urinary catheter 272.

The container 270 comprises a single molded piece formed by two identical halves 274a, 274b connected with a living hinge 276. Each of the halves 274a, 274b is defined by a generally hemi-cylindrical trough formed by outer walls 277 that define a longitudinal partial cavity, and a pair of half bulkheads 278a, 278b extending laterally or transversely across the channel. Each of the half bulkheads 278a, 278b defines a central indent 279 of semi-circular configuration. Although not shown, a tapered inlet on the proximal side of each of the indents 279 may be added. When the two halves 274a, 274b are brought together as indicated by the arrows by pivoting them about the living hinge 276, the half bulkheads 278a, 278b align to form full bulkheads such that the indents 279 together form circular through bores. Desirably, the two halves 274a, 274b are sealed together at their points of contact and then pressure tested before adding the cap.

The assembly of FIGS. 25A and 25B shows the catheter 272 passing through the conjoined bulkheads 278a, 278b with a distal end located in an empty distal cavity of the container 270. Gel G provided in a middle cavity 280 between the two bulkheads 278a, 278b allows the catheter 272 to be coated when it is withdrawn from the container. In a manner similar to that described above, the gel may be added prior to or after assembly of the container 270. For example, FIG. 24A shows the catheter 272 resting in the lower half 274b of the container and gel G provided in both partial cavities between the bulkheads. The two halves 274a, 274b can then be brought together and sealed, and the cap added for sterility. Alternatively, the container 270 may be assembled without the catheter 272, at which point a predetermined volume of gel G may be injected via the through bore in the proximal bulkhead 278a into the middle cavity 280.

FIG. 26A is an exploded longitudinal sectional view of two components 282a, 282b of a rigid main body of a urinary catheter sterile container. A proximal component 282a has a generally tubular outer wall 283 extending longitudinally with a transverse bulkhead 284 disposed transversely across a midsection. The bulkhead 284 has a through bore 285 with a plurality of inwardly-extending axial ribs 286, as best seen in FIG. 26B. A distal component 282b has a generally conical exterior shape with a tapered entry aperture 287 leading to a hollow cavity. An assembled sterile container 288 is seen in FIG. 27B with the two components 282a, 282b coupled together and aligned along a longitudinal axis, with an end cap 289 housing a urinary catheter 290. When coupled together, a middle cavity 291 filled with gel G is formed between the bulkhead 284 of the proximal component 282a and the entry aperture 287 of the distal component 282b. A narrow end of the tapered entry aperture 287 is sized approximately the same as the exterior diameter of the tube of the catheter 290 so the gel G does not extend into the cavity of the distal component 282b.

FIG. 27A is a longitudinal sectional view of the proximal component 282a pre-assembled with the urinary catheter 290 and lubricating gel G. This pre-assembly may then be coupled to the distal component 282b, and the end cap 289 added to complete the container 288. In this way, the gel G can easily be added into the middle cavity 291. A proximal end 292 of the distal component 282b mates with a distal end of the proximal component 282a. In the illustrated embodiment, the distal component 282b has a stepped proximal end 292 which fits closely within the wall of the middle cavity 291 of the proximal component 282a, although other mating arrangements are contemplated. Once again, the two components may be secured together by various welding or gluing methods. When withdrawing the catheter 290, the axial ribs 286 in the through bore 285 of the bulkhead 284 facilitate even distribution of lubricant gel G on the outer surface of the tube of the catheter 290.

Figure 28:
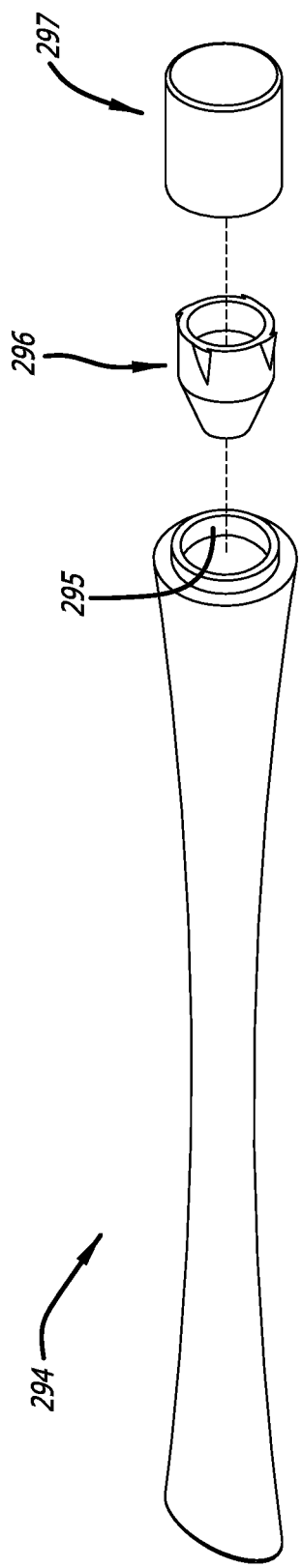
FIGS. 28 and 29 are exploded views of a still further sterile container for urinary catheters having internal bulkheads and shown with one- and two-part rigid main bodies, respectively.
Figure 29:
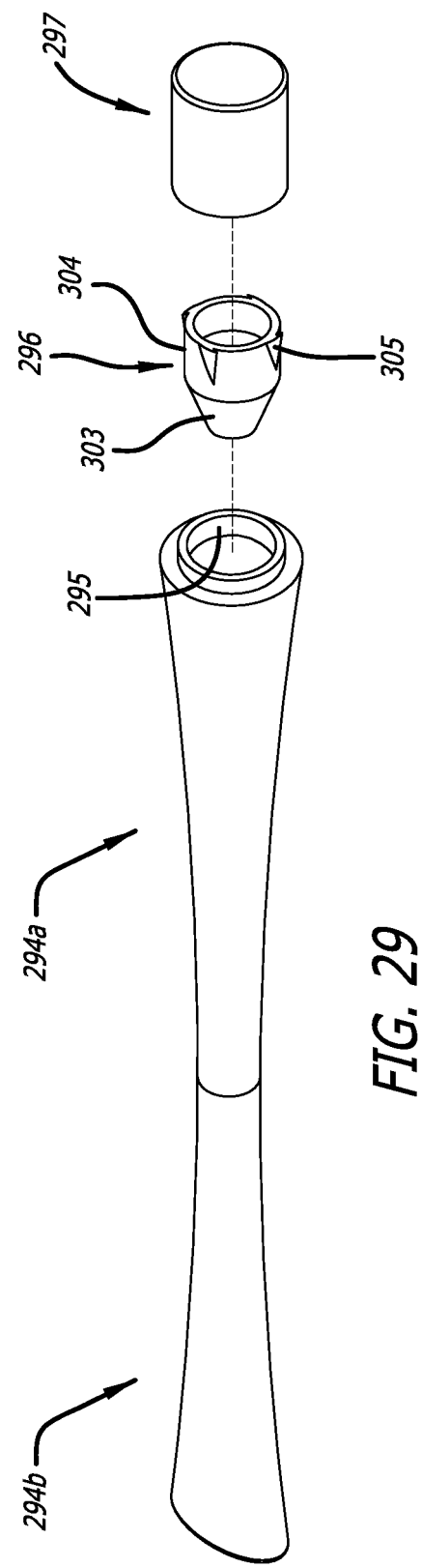

FIGS. 28 and 29 are exploded views of a still further sterile container for urinary catheters having internal bulkheads and shown with one- and two-part rigid main bodies, respectively. FIG. 28 illustrates a single-component hollow main body 294 having a generally hourglass-shaped exterior, with a closed distal end opposite an open proximal mouth 295. A tapered bulkhead 296 fits into the interior of the main body 294 through the proximal mouth 295, and after insertion of a urinary catheter (not shown), an end cap 297 is added for sterility. FIG. 29 illustrates a nearly identical assembly, though the main body is formed by a combination of a proximal component 294a and a distal component 294b.

Now with reference to FIG. 30, a longitudinal sectional view of the two-part rigid main body of the sterile container of FIG. 29 shows a distal bulkhead 298 formed at the junction between the proximal component 294a and a distal component 294b. Proximal and distal cavities are formed on either side of the distal bulkhead 298, each of which is tapered to mirror the hourglass outer shape of the container. FIG. 30A is an enlargement of the distal bulkhead 298 and FIG. 31 is a side view of the sterile container shown assembled with a urinary catheter 300 and the proximal bulkhead 296. The sterile end cap 297 (FIG. 29) will also be added to enclose urinary catheter 299 therein.

The distal bulkhead 298 defines a through bore 301 having a luminal diameter about the same as an exterior diameter of the tube of a urinary catheter. In the illustrated embodiment, the bulkhead 298 is defined by a narrowed or stepped distal end of the proximal component 294a, which also defines a tapered entry 302 for ease in insertion of the urinary catheter therethrough. Of course, the bulkhead 298 may also be defined by a narrowed or stepped proximal end of the distal component 294b, the bulkhead simply being a narrowing at the junction between the two components. The proximal bulkhead 296 may be similar to those described above, such as for example the bulkheads 250 of FIG. 21. In the illustrated embodiment, the proximal bulkhead 296 has a generally tubular body formed by an outwardly conical distal end 303 in series with an outwardly cylindrical proximal end 304. A series of flexible fins 305 extend outward from the proximal end 304, and help retain the bulkhead 296 within the tapered cavity defined within the proximal component 294a.

As with earlier versions, the container components 294a, 294b are desirably molded of polypropylene and coupled together using a variety of welding or gluing methods. The completed assembly of FIG. 31 (minus the endcap 297) defines a middle cavity 306 between the proximal bulkhead 296 and the distal bulkhead 298. The cavity 306 may be filled with gel G before or after addition of the urinary catheter 300, as explained above. Preferably, the proximal bulkhead 296 is first pre-assembled around the urinary catheter 300, and gel G applied around the tube of the catheter just distal to the bulkhead. The pre-assembly is then inserted into the hollow container formed by the components 294a, 294b until the proximal bulkhead 296 is wedged within the tapered interior thereof.

FIGS. 32A-32B are side elevational views of two different sterile containers 310 for intermittent urinary catheters. The two containers 310 are identical except for different cap closures. The containers 310 include a generally tubular main body 312 having a lower closed end opposite an upper open end. A closed cap 316 engages the upper open end of each main body 312 to seal the interior thereof. In FIG. 32A, the cap 316 engages the main body through friction or with interfering ribs, as described above, while in FIG. 32B the cap 316 has a series of internal threads which engage external threads on the mouth of the main body.

The tube of the catheter 314 extends down into the hollow interior defined within each of the main bodies 312. The tube is smaller than the inner diameter of the hollow interiors so as to form concentric spaces 318 therebetween. A lubricating gel (not shown) is provided within the spaces 318 prior to insertion of the catheter 314, such that when the user removes the catheter it is gel coated and ready for use. It should be noted that the inner lumen of the main body 312 is substantially cylindrical down to a rounded dead end 313, but has a tapered upper portion 315 opening to the upper mouth. The catheter 314 has a tapered outlet or funnel 317 which fits closely within the upper portion 315. Additionally, an elastomeric seal or collar 319 is provided at the bottom of the funnel 317 (and is preferably molded therewith) which is sized to engage the cylindrical portion of the main body lumen. The collar 319 thus seals any gel within the concentric space 318.

FIGS. 33A-33B are side elevational views of a further sterile container 320 for intermittent urinary catheters. As before, the container 320 includes a generally tubular yet inwardly-tapered main body 322 having a lower closed end opposite an upper open end and a hollow interior. A closed cap 326 engages the upper open end of each main body 322 to seal the interior thereof through friction, with interfering ribs, or with mating threads as shown.

The tube of the catheter 324 extends down into the hollow interior defined within the main body 322. The tube is smaller than the inner diameter of the hollow interior so as to form a concentric space 328 therebetween. A lubricating gel (not shown) is provided within the space 328 prior to insertion of the catheter 324, such that when the user removes the catheter it is gel coated and ready for use. The inwardly-tapered main body 322 and inner space 328 constrict in the middle portion and the lubricating gel is deposited only in the distal end of the hollow interior of the main body 322 which helps reduce the amount of gel that is removed upon catheter removal, thus helping to reduce mess. It should be noted that the inner lumen of the main body 322 has a shallow hourglass shape down to a rounded dead end 323, but has a tapered upper portion 325 opening wider to the upper mouth. The catheter 324 has a tapered outlet or funnel 327 which fits closely within the upper portion 325 and is in fluid communication with the catheter lumen. Additionally, an elastomeric seal or collar 329 is provided at the bottom of the funnel 327 (and is preferably molded therewith) which is sized to engage the narrowing portion of the main body lumen. The collar 329 thus seals any gel within the concentric space 328. The main body 322 further includes an angled distal end 330 through which the distal tip of the catheter 324 can be viewed. The angled distal end 330 may also be squared off, depending on manufacturing constraints.

FIG. 34 is a side elevational view of a still further sterile container 340 for an intermittent urinary catheter. The outer components of the container 340 include a tapered main body 342 which may be closed by a cap 344, such as with mating threads. FIG. 35 is a sectional view of a catheter having an outlet 350 on the proximal end of a catheter tube 352 which is inserted within a generally tubular gel holder 354 with a closed distal end. The assembly of the gel holder 354 and catheter is seen placed within the hollow interior of the main body 342 of the container 340 in FIG. 34. In a preferred embodiment, the gel holder 354 has a tapered configuration which fits closely within the tapered main body 342. An outwardly projecting circular flange 356 at the top of the tapered gel holder 354 is sized to contact the gradually narrowing inner walls of the main body 342 in an interference fit so as to secure the gel holder within the main body. Alternatively, the flange 356 may be forced past a small inward circular rib (not shown) within the gel holder 354 to ensure the gel holder 354 remains within the main body 342.

The circular flange 356 defines a central opening through which the catheter tube 352 is inserted into an inner cavity of the gel holder. An annular seal or collar 357 at the base of the catheter outlet 350 that is larger than the central opening helps maintain the gel G within the cavity of the gel holder 354. As with certain other embodiments described herein, a concentric space is provided around the catheter tube 352 within the inner space which may be filled with lubricant gel G. The central opening in the circular flange 356 has an inner diameter A, shown in FIG. 35A which is slightly larger than the outer diameter D of the catheter tube 352. When the user withdraws the catheter from within the gel holder 354, gel G coats the exterior of the catheter tube 352, as seen in FIG. 36. The spacing created between the catheter tube 352 and the central opening wipes off a majority of the gel G which might otherwise stick to the tube but leaves a thin coating thereon. In one embodiment, the diameter D of the catheter tube 352 ranges between 8-16 French, or between about 2.7-5.3 mm (3 Fr=1 mm). The diameter A of the central opening is desirably about 1-2 mm larger than the corresponding catheter tube diameter, or between 3.7-7.3 mm. Since the entirety of the inner cavity of the gel reservoir 354 is filled with gel G, the distal tip of the catheter to 352 emerges covered with gel as well.

Radial score lines 358 allow for molding of the gel holder 354. There is an undercut design for the flange 356 and the score lines 358 allow for removal of the mold core by allowing the flange to flex open during part ejection.

Figure 37:
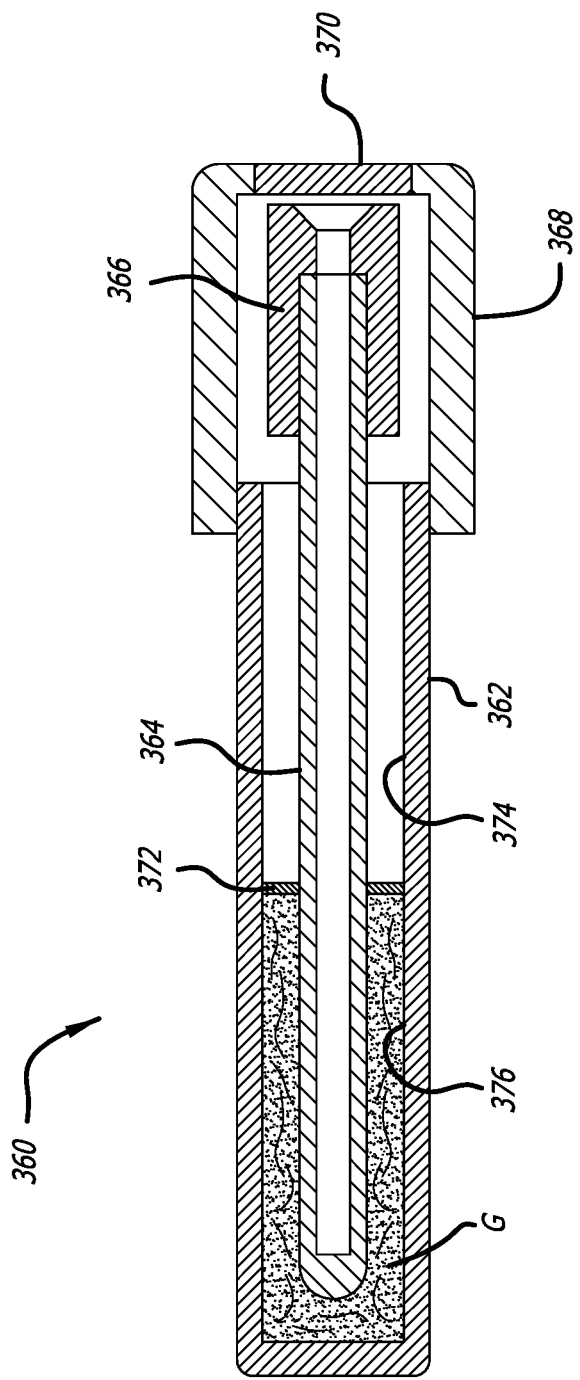
FIG. 37 is a longitudinal sectional view through an alternative sterile container for an intermittent urinary catheter.

FIG. 37 is a longitudinal sectional view through an alternative sterile container 360 for an intermittent urinary catheter. In this version, the container 360 includes a generally tubular main body 362 closed at one end and open at the other. The catheter tube 364 inserts within the open end of the main body 362 such that an outlet 366 remains outside. A cap 368 is then secured around the main body 362 using any of the means described herein. The cap 368 preferably has a solid end 370.

A barrier or divider wall 372 segregates the inner volume of the main body 362 into a proximal first section 374 and a distal second section 376. The divider wall 372 is a central aperture sized slightly larger than the outer diameter of the catheter tube 364, such that the tube is passed through the aperture and a distal portion resides within the second section 376, which may be filled with gel G. The divider wall 372 thus helps retain the gel G in the distal end of the closed main body 362 to reduce mess when withdrawing the catheter. As the catheter is withdrawn, it emerges coated with gel G along its distal length and distal tip. The difference in diameter between the aperture of the divider wall 372 and the outer diameter of the catheter tube 364 may be the same as described above for the gel holder 354 of FIG. 35. That is, the diameters A and B may be the same in the embodiment of FIGS. 37 and 37A-37B.

Figure 37A:
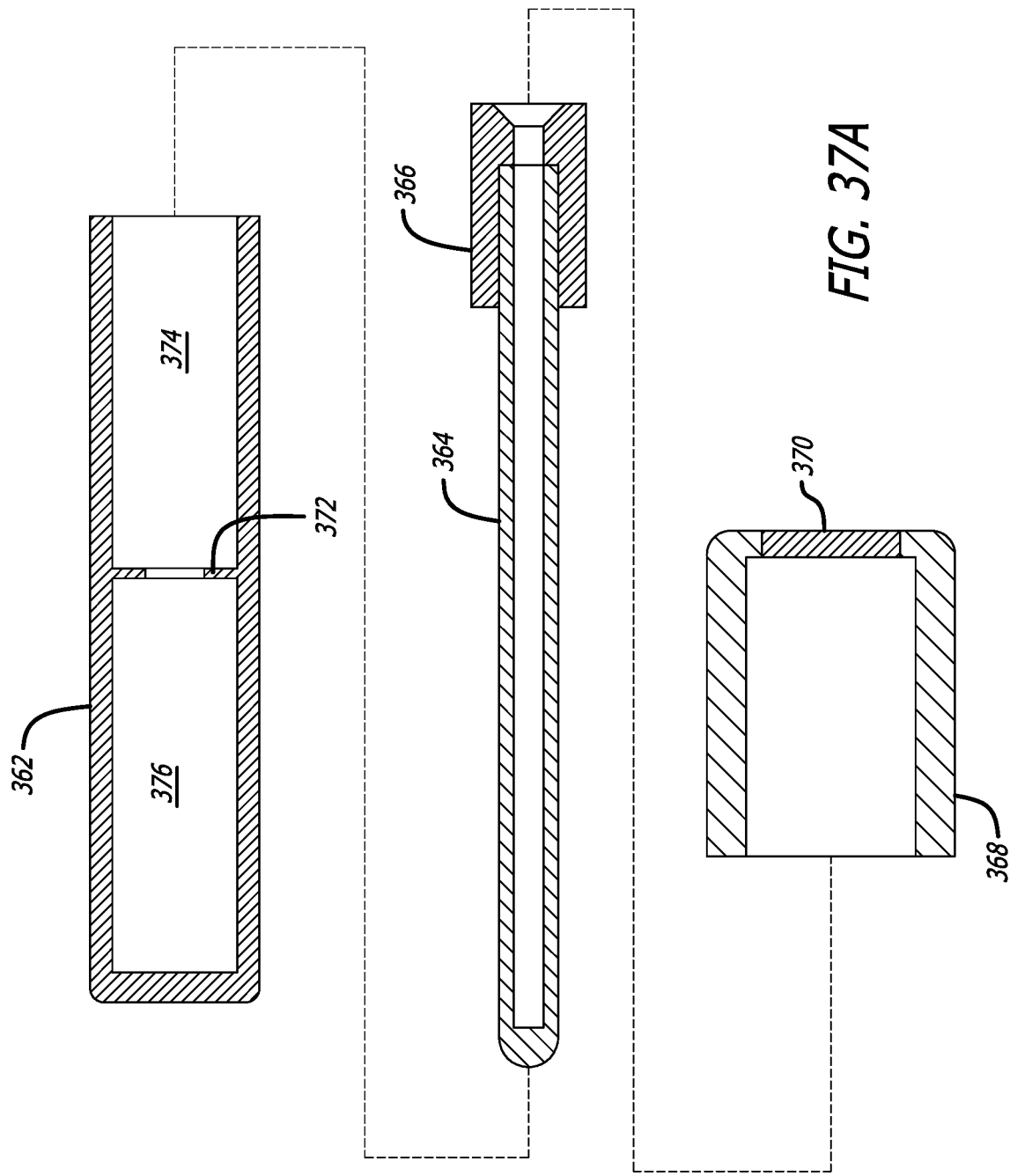

FIGS. 37A-37B are exploded views of alternative configurations of the components of the sterile container 360 of FIG. 37. In the first embodiment of FIG. 37A, the divider wall 372 is formed by a molded bulkhead within the main body 362. Conversely, in the embodiment shown in FIG. 37B, the divider wall 372 is a removable annular disk. This embodiment is slightly easier to manufacture, though accommodation must be made to retain the disk 372 within the main body 362. In one embodiment, the annular disk 372 is retained within the inside of the main body 362 with adhesive. In another embodiment the disk is held in place by a snap fit into a ring-shaped receiving cavity.

In each of the embodiments shown in FIGS. 8-37, the catheter can have a length in a range of between about 10-15 cm, which makes the catheter especially suited for use with female patients. The entire container preferably has a length of no more than 1-2 cm longer than the catheter. So, a 10 cm long catheter would be packaged in a container of between 11-12 cm, and a 15 cm long catheter would be packaged in a container of between 16-17 cm.

Throughout this description, the embodiments and examples shown should be considered as exemplars, rather than limitations on the apparatus and procedures disclosed or claimed. Although many of the examples presented herein involve specific combinations of method acts or system elements, it should be understood that those acts and those elements may be combined in other ways to accomplish the same objectives. Acts, elements and features discussed only in connection with one embodiment are not intended to be excluded from a similar role in other embodiments.

It is claimed:

1. A urinary catheter package, comprising:
   a urinary catheter having an elongated flexible tube defining a closed distal tip with one or more flow openings formed in an adjacent sidewall thereof, and a proximal outlet attached to a proximal end of the tube and having a through passage in communication with a lumen of the tube;
   a rigid generally tubular main body having a distal closed end opposite a proximal open mouth along a longitudinal axis and defining within a hollow interior;
   a pair of spaced apart internal barriers including a distal barrier and a proximal barrier both positioned within the main body and extending transversely across the hollow interior and defining a gel cavity therebetween for receiving lubricating gel, each barrier having a central throughbore sized to permit passage of the tube of the catheter, with the throughbore of the distal barrier being sized approximately the same as the tube to substantially prohibit gel from passing distally past the distal barrier, wherein the tube of the urinary catheter may be inserted through the open mouth of the main body and into the hollow interior through both barriers such that at least a portion of the proximal outlet remains outside the main body, and such that the urinary catheter may be withdrawn from the main body and lubricating gel from the gel cavity remains on the tube; and
   a rigid cap secured to the open mouth of the main body so as to seal the urinary catheter within the hollow interior in a sterile manner;
   wherein the distal barrier is formed by a molded feature within the main body and the proximal barrier is formed by an insert separate from the main body.

2. The urinary catheter package of claim 1, wherein external structural features of the insert that forms the proximal barrier and/or internal structural features of an inner wall of the main body are configured so that the insert may be inserted to a predetermined depth within the hollow interior spaced from the distal barrier.

3. The urinary catheter package of claim 2, wherein the inner wall of the main body tapers inward from the proximal open mouth in a distal direction such that the insert may be pressed into the hollow interior to the predetermined depth before interference between the insert and the inner wall halts further advancement.

4. The urinary catheter package of claim 2, wherein the insert has a plurality of flexible fins on its exterior which form an interference fit with the inner wall of the main body.

5. The urinary catheter package of claim 1, wherein the main body is formed by a proximal component coupled in series to a distal component at a junction, and wherein the distal barrier is formed by a narrowing at the junction leading to a hollow cavity in the distal component.

6. The urinary catheter package of claim 1, wherein the insert comprises a generally tubular member, and wherein external structural features of the tubular member and/or internal structural features of an inner wall of the main body are configured so that the tubular member may be inserted to predetermined depth within the hollow interior spaced apart from the molded feature that forms the distal barrier.

7. The urinary catheter package of claim 6, wherein the insert has a plurality of flexible fins on its exterior which form an interference fit with the inner wall of the main body.

8. The urinary catheter package of claim 1, wherein the proximal barrier has a tapered lead-in to the throughbore therein.

9. The urinary catheter package of claim 8, wherein the distal barrier also has a tapered lead-in to the throughbore therein.

10. The urinary catheter package of claim 1, wherein the proximal barrier has a plurality of inwardly-projecting axial ribs within the throughbore therein that contact and center the tube of the catheter and ensure an even layer of gel is applied to the tube upon withdrawal past the proximal barrier.

11. The urinary catheter package of claim 1, wherein the catheter has a length of between about 10-15 cm, and the catheter package has a length of no more than 1-2 cm longer than the catheter.

12. The urinary catheter package of claim 1, wherein the main body has an hourglass shape such that a central portion of the main body is narrower than either end of the main body.

13. A urinary catheter package, comprising:
    a urinary catheter comprising an elongated flexible tube;
    a rigid generally tubular main body having a proximal end portion including an open mouth, a distal end portion opposite the proximal end portion, and an intermediate portion positioned between the distal end portion and the proximal end portion, wherein an inner diameter of the intermediate portion is less than an inner diameter of the proximal end portion;
    a pair of spaced apart internal barriers including a distal barrier and a proximal barrier, wherein both the distal barrier and the proximal barrier are positioned within the main body such that a gel cavity is defined between the pair of spaced apart internal barriers, wherein each of the proximal barrier and the distal barrier comprises a corresponding and respective aperture sized to permit passage of the tube, and wherein the aperture of the distal barrier is configured to conform to the tube to discourage gel from passing distally beyond the distal barrier; and
    a rigid cap secured to the open mouth of the main body so as to seal the urinary catheter within the main body in a sterile manner.

14. The urinary catheter package of claim 13, wherein the main body comprises a distal body component and a proximal body component; and
    wherein a proximal portion of the distal body component is matingly engaged with a distal portion of the proximal body component.

15. The urinary catheter package of claim 14, wherein the intermediate portion comprises the proximal portion of the distal body component and the distal portion of the proximal body component.

16. The urinary catheter package of claim 14, wherein the distal portion of the proximal body component comprises a molded feature defining the distal barrier.

17. The urinary catheter package of claim 16, further comprising an insert separate from the main body, the insert defining the proximal barrier.

18. The urinary catheter package of claim 13, wherein the distal barrier is formed by a molded feature within the main body.

19. The urinary catheter package of claim 13, further comprising an insert separate from the main body, the insert defining the proximal barrier.

20. The urinary catheter package of claim 19, further comprising a plurality of flexible fins configured to facilitate an interference fit between the insert and an inner wall of the main body.

21. The urinary catheter package of claim 13, wherein the main body is fluted such that the intermediate portion is narrower than each of the distal end portion and the proximal end portion.

\* \* \* \* \*